US008604223B2

(12) United States Patent
Selifonov et al.

(10) Patent No.: US 8,604,223 B2
(45) Date of Patent: Dec. 10, 2013

(54) METHOD OF MAKING KETALS AND ACETALS

(75) Inventors: Sergey Selifonov, Plymouth, MN (US); Scott D. Rothstein, Sauk Rapids, MN (US); Brian D. Mullen, Plymouth, MN (US)

(73) Assignee: Segetis, Inc., Golden Valley, MN (US)

( * ) Notice: Subject to any disclaimer, the term of this patent is extended or adjusted under 35 U.S.C. 154(b) by 0 days.

(21) Appl. No.: 12/757,065

(22) Filed: Apr. 9, 2010

(65) Prior Publication Data

US 2010/0292491 A1    Nov. 18, 2010

Related U.S. Application Data

(63) Continuation of application No. PCT/US2008/079083, filed on Oct. 7, 2008.

(60) Provisional application No. 60/960,629, filed on Oct. 9, 2007, provisional application No. 61/048,339, filed on Apr. 28, 2008.

(51) Int. Cl.
*C07D 317/20* (2006.01)
(52) U.S. Cl.
USPC .......................................................... 549/454
(58) Field of Classification Search
USPC .......................................................... 549/454
See application file for complete search history.

(56) References Cited

U.S. PATENT DOCUMENTS

| | | | |
|---|---|---|---|
| 1,934,309 A | 10/1927 | Hoover | |
| 2,008,720 A | 7/1935 | Lawson | |
| 2,260,261 A | 1/1940 | Morey | |
| 2,556,135 A | 6/1951 | Croxall et al. | |
| 2,654,723 A | 10/1953 | Greene | |
| 3,658,789 A | 4/1972 | Fried | |
| 4,792,411 A | 12/1988 | Walsh | |
| 4,923,891 A * | 5/1990 | Deason et al. | 514/433 |
| 5,095,098 A | 3/1992 | McLain et al. | |
| 5,202,413 A | 4/1993 | Spinu et al. | |
| 5,917,059 A | 6/1999 | Bruchmann et al. | |
| 5,998,092 A | 12/1999 | McCulloch et al. | |
| 6,528,025 B1 | 3/2003 | Boesch et al. | |
| 6,806,392 B2 | 10/2004 | Boesch et al. | |
| 6,828,272 B2 | 12/2004 | Wiegner et al. | |
| 2003/0167681 A1 | 9/2003 | Delgado Puche | |
| 2004/0024260 A1 | 2/2004 | Winkler et al. | |
| 2008/0242721 A1 | 10/2008 | Selifonov | |

FOREIGN PATENT DOCUMENTS

| | | |
|---|---|---|
| CA | 1000285 | 11/1976 |
| DE | 3220035 A1 | 1/1983 |
| DE | 10036423 A1 | 3/2001 |
| EP | 0308956 A2 | 3/1989 |
| EP | 0507190 A1 | 3/1992 |
| FR | 1445013 | 7/1966 |
| JP | 4217972 | 8/1992 |
| JP | 2006143702 A | 6/2006 |
| SU | 722912 | 3/1980 |
| WO | 9412489 A1 | 6/1994 |
| WO | 2004099173 A1 | 11/2004 |
| WO | 2005097723 A2 | 10/2005 |
| WO | 2005097724 A1 | 10/2005 |
| WO | WO2007/062118 A2 | 5/2007 |
| WO | 2008089463 A2 | 7/2008 |
| WO | 2008098375 A1 | 8/2008 |
| WO | WO2009/032905 A1 | 3/2009 |
| WO | 2009048874 A1 | 4/2009 |
| WO | WO2010/036884 A1 | 4/2010 |
| WO | 2011140644 A1 | 11/2011 |

OTHER PUBLICATIONS

Product Data Sheet for Amberlite IR120 H, obtained from http://www.dow.com/products/product_detail.page?displaymode=highlight&product=1120974 on Mar. 9, 2012.*
Boehm, R., "Knowledge on cyclic ketals. Part 11: Synthesis of some new derivatives and separation of their isomers," Pharmazie 36(5): 329-330 (1981).
Brigl, et al., "The Reaction of the Pyruvic Acid with Glycerin," Annalen der Chemie 476: 215-232 ( In German Only).
Briol, et al., "Reaction of pyroracemic acid with glycerol," Ann. 476: 215-232 (1929).
Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).
Chirila, T., "Pent-and hexatomic cycloacetal esters. Synthesis and characterization of some 2-Carbalkoxymethyl-1,3-dioxolanes (dioxanes)," Revista de Chimie 28: 730-733 (1977).
Chopade, et al., "Acetalization of ethylene glycol with formaldehyde using cation-exchange resins as catalysts: batch versus reactive distillation," Reactive and Functional Polymers 34: 37-45 (1997).
Clarkson, et al., "Continuous Reactor Technology for Ketal Formation: An Improved Synthesis of Solketal," Organic Process Research & Development 5: 630-635 (2001).
Culling, et al., "Synthesis of Levulinic Ketals with Furfuryl Alcohol as Raw Material," Journal of Huagiao University (Nature Science) 23(3): 257-259 (2002) (English Translation).
Deutsch, et al., Investigations on heterogeneously catalysed condensations of glycerol to cyclic acetals, Journal of Catalysis 245: 428-435 (2007).

(Continued)

Primary Examiner — Wu-Cheng Winston Shen
Assistant Examiner — Karen Cheng
(74) Attorney, Agent, or Firm — Cantor Colburn LLP

(57) ABSTRACT

The reaction of alcohols with oxocarboxylates to form acetals or ketals is catalyzed by unexpectedly low levels of protic acids. By employing low acid catalyst levels compared to amounts conventionally used, rapid formation of acetal or ketal is facilitated while the formation of oxocarboxylate esters is minimized. Further employing a significant molar excess of oxocarboxylate in conjunction with low acid catalyst level gives rise to the rapid and clean formation of acetals and ketals from oxocarboxylates and alcohols.

46 Claims, 3 Drawing Sheets

(56) References Cited

OTHER PUBLICATIONS

Di Serio, et al., Transesterification of Soybean Oil to Biodiesel by Using Heterogeneous Basic Catalysts, Ind. Eng. Chem. Res. 45: 3009-3014 (2006).
DuPont Tyzor Organic Titanates Technical Note—Direct Esterification, 3 pages (2001).
DuPont Tyzor Organic Titanates Technical Note—Transesterification, 3 pages (2001).
Gelas, et al., "Synthese du 4-oxo et de 4-hydroxy-3,6,8-trioxabicyclo[3.2.1]octanes," Carbohydrate Research 30(1): 21-34 (1973) (with English abstract).
Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).
Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).
Haskelbhrg, L., "The preparation of glycerol esters of amino acids," Compt. rend. 190270-190272 (1930).
Hegde, et al., "The Kinetics and Thermodynamics of Bicyclic Ketal Formation: An Application to the Synthesis of the Zaragozic Acids," Tetrahedron 53(32): 11179-11190 (1997).
Hoydonckx, et al., "Esterification and transesterification of renewable chemicals," Topics in Catalysis 27(1-4): 83-96 (2004).
Imwinkelried, et al., "Diisopropyl (2S,3S)-2,3-0-Isopropylidenetartrate [1,3-Dioxolane-4,5-dicarboxylic acid, 2,2-dimethyl-, bis(1-methylethyl)ester, (4R-trans)-]," Organic Syntheses 8: 201-230 (1993).
Li, et al., "Montmorillonite Clay Catalysis. Part 2. An Efficient and Convenient Procedure for the Preparation of Acetals Catalysed by Montmorillonite K-10," J. Chem Research (S) 26-27 (1997).
Lukes, Robert M., Preparation of Methyl Esters Containing the 1,3-Dioxane or 2,4,8,10-Tetroxaspiro[5.5]undecane Structure by Ketal Exchange, 26:2515-2518 (1961).
Meher, et al., "Technical aspects of biodiesel production by transesterification—a review," RSER 194: 1-21 (2004).
Meltzer, et al., "2,2-Disubstituted 1,3-Dioxolanes and 2,2-Disubstituted 1,3-Dioxanes," JOC 25: 712-715 (1960).
Miller, et al., "Biorenewable Fuels and Chemicals via Reactive Distillation," Midtech Midland, May 11, 2006 (Powerpoint Presentation).
Nagata, et al., "Synthesis and Applications of [2-Methyl-2(oxoalkyl)-1,3-dioxolan-4-yl]methyl Acrylates for Photocrosslinking Agent," Osaka Kogyo Gijutsu Shikensho Kiho 37(1): 8-16 (1986).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Newman, et al.,"Kinetic and Equilibrium Studies of Cyclic Ketal Formation and Hydrolysis," The Journal of the American Oil Chemist's Society 80: 6350-6355 (1958).
Patel, et al., "Ketalization of ketones with diols catalyzed by metal (IV) phosphates as solid acid catalysts," Journal of Molecular Catalysis A: Chemical 194: 267-271 (2003).
Piantadosi, et al., "The Preparation of Cyclic Glycerol Acetals by Transacetalation," Journal of the American Chemical Society 80: 6613-6617 (1958).
Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).
Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).
Stern, et al., "On Hydroboration of 5-Dimethylamino-3-Methyl-1-Pentene and 5-Dimethylamino-3,3-Dimethyl-1-Pentene," Czechoslov. Chem. Commun. 39: 3538-3547 (1974).
Wang, et al., "An efficient procedure for protection of carbonyls catalyzed by sulfamic acid," Journal of Molecular Catalysis A: Chemical 233: 121-126 (2005).
Wedmid, et al., "Long-Chain Stereomeric 2-Alkyl-4-methoxycarbonyl-1,3-dioxolanes in Glycerol Acetal Synthesis," J. Org. Chem. 42(22): 3624-3626 (1977).
Wood, et al., "Cyclic polyesters: 1. Preparation by a new synthetic method, using polymer-supported reagants," Polymer 34(14): 3052-3058 (1993).
Xu, et al., "The monoblocking of symmetrical diketones on insoluble polymer supports," Can. J. Chem. 61: 1405-1409 (1983).
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Zhang, et al., "Synthesis of Ketals of 4-Oxopentanoates," Lanzhou Daxue Xuebao, Ziran Kexueban 30(2): 66-70 (1994).
Atofina Publication No. A-70-1 ( © 2001 by Atofina Chemicals, Inc. of Philadelphia, PA; available on the internet at http://staging.arkemainc.com/literature/pdf/405.pdf, 5 pages.
Carey, Francis A. and Sundberg, Richard J., Advanced Organic Chemistry, Second Edition, Part B: Reactions and Synthesis Plenum Press, NY (1983) p. 539-552.
Clerici, Angelo, et al., "Efficient Acetalisation of Aldehydes Catalyzed by Titanium Tetrachloride in a Basic Medium", Tetrahedron 54 (1998) p. 15679-15690.
Deslongchamps, Pierre, et al., "The total synthesis of (+)-ryanodol. Part II. Model studies for rings B and C of (+)-anhydroryandol. Preparation of a key Pentacyclic intermediate", Can. J. Chem. 68 (1990) p. 127-152.
Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.
International Search Report PCT/US2008/07983, mailed Jan. 22, 2009, 3 pages.
Meskens, Frans A. J., Methods for the Preparation of Acetals from Alcohols or Oxiranes and Carbonyl Compounds, Synthesisn (1981) 501-522.
Ono, Daisuke, et al., "Preparation, Surface-Active Properties and Decomposition Profiles of a New "Soap" Bearing a 1-3-Dioxolane Ring", J. Am. Oil Chem. Soc. 70(1), (1993) p. 29-36.
Otera, Junzo, Esterificaton, Methods, Reactions, and Applications, Wiley-VCH Verlag GmbH & Co., (2003) p. 1-19.
Pasto, D. J. and Serve, M. P., "Neighboring Group Participation by Carbonyl Oxygen", J. Amer. Chem. Soc., 87(7) (1965) 1515-1521.
Preliminary Report on Patentability for PCT/US2008/079083, dated Jan. 12, 2010, 16 pages.
Written Opinion of the International Searching Authority for PCT/US2008/079083, mailed Jan. 22, 2009, 6 pages.
Kaihara, et al., "Synthesis and Properties of Poly[poly(ethylene glycol)-co-cyclic acetal] Based Hydrogels", Macromolecules, 40, 2007, pp. 7625-7632.
Otera, J., Esterification. Methods, REactions and Applications, Part One, Wiley, 2010, pp. 1-51.
Smith, R., "Chemical Process Design and Integration", Centre for Process Integration, School of Chemical Engineering and Analytical Science, Univ. of Manchester, John Wiley & Sons, Ltd., 2005, 85 pages, Chapters 7, 11, and 13.

\* cited by examiner

METHOD OF MAKING KETALS AND ACETALS

CROSS-REFERENCE TO RELATED APPLICATION

This application is a continuation of prior PCT Application No. PCT/US2008/079083 having an International Filing Date of Oct. 7, 2008, which claims benefit under 35 U.S.C. §119(e) to U.S. Provisional Patent Application No. 60/960,629, filed on Oct. 9, 2007, which is incorporated by reference in its entirety herein; this application further claims the benefit of U.S. Provisional Patent Application No. 61/048,339, filed on Apr. 28, 2008, which is incorporated by reference in its entirety herein.

TECHNICAL FIELD

The present disclosure relates to a method for the preparation of ketal and acetal compounds by the acid-catalyzed reaction of alcohols with keto acids, semialdehydes, and esters thereof.

BACKGROUND

Keto acids, semialdehydes, and their esters contain two carbonyl moieties, a carboxylate moiety and an oxo moiety. The oxo moiety in keto acids is a ketone, and the oxo moiety in semialdehydes is an aldehyde. Alcohols may react with one or both types of carbonyl moieties. Reaction with the oxo moiety leads to ketal or acetal formation; reaction with the carboxylate moiety leads to ester formation or transesterification. Where it is desirable to react an alcohol with one but not the other carbonyl moiety, selectivity is required to provide good yield of the desired product.

It can be advantageous to react an alcohol with a keto acid, semialdehyde, or ester thereof to form a ketal or an acetal. However, the carboxylic acid or ester moiety present on keto acid and semialdehyde structures presents an additional site for reaction of an alcohol. Where ketal or acetal formation is sought, it is desirable to exclude esterification or transesterification reactions.

The reaction rate of alcohols with oxo moieties to form ketals and acetals is generally slow; for this reason such reactions are typically carried out in the presence of an acid catalyst, most typically homogeneous catalysis is employed using a protic acid (Brønsted-Lowry acid). For example, sulfuric acid, hydrochloric acid, phosphoric acid, p-toluenesulfonic acid and mixtures of these are known to catalyze ketal and acetal formation. Lewis acids, e.g. aprotic acids, have also been used to catalyze ketal and acetal formation from alcohols. For example, Clerici et al., *Tetrahedron* 54, 15679-90 (1998) employ titanium tetrachloride to affect the reaction of methanol with various aldehydes in the presence of ammonia or amine However, the same catalysts employed in ketalization and acetalization reactions are also well known to be catalysts for esterification and transesterification. The conventional amounts of acid employed in the two types of reactions are in the same range when molar equivalents of acid are calculated based on a limiting reagent. Therefore, catalysis of the reaction of an alcohol with a keto acid, semialdehyde, or ester thereof by an acid catalyst can result in esterified side products. For example, three moles of an alcohol such as methanol could react with one mole of a keto acid, such as pyruvic acid, in the presence of a sulfuric acid to yield the dimethyl ketal of methyl pyruvate, or methyl 2,2-dimethoxypropionate.

It is well known that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" $2^{nd}$ ed., © 1983, Plenum Press, NY, N.Y., p. 544). The 1,2 and 1,3 configurations of hydroxyl groups on a hydrocarbon chain are shown below as (a) and (b), respectively.

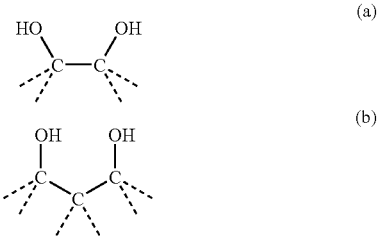

Diols such as 1,2-ethane diol (ethylene glycol) and 1,3 propanediol (propylene glycol) are examples of such polyols. Diols having a 1,2 hydroxyl group configuration will form dioxolanes when reacted with ketone or aldehyde moieties, while 1,3 diols will form dioxanes. Higher polyols, such as triols and tetrols, including polymeric polyols, can be used to form cyclic ketals as well when at least two of the polyol hydroxyl groups are in the 1,2 or 1,3 configuration. Cyclic ketal formation is also typically catalyzed by acids.

Where diols and higher polyols are employed in a ketalization or acetalization reaction of a keto acid, semialdehyde, or an ester thereof, side products can form in addition to the side products resulting from a simple esterification or transesterification. The presence of an acid catalyst can increase the number and concentration of these side products. For example, a diol can undergo esterification or transesterification with the carboxyl moiety of a keto acid, semialdehyde, or ester thereof. The resulting diol ester will have a residual hydroxyl moiety available for either a ketalization/acetalization reaction or further esterification/transesterification. In another example, a triol molecule can react with a keto ester molecule to form the cyclic ketal ester; the cyclic ketal ester will have a residual hydroxyl moiety. Thus, the cyclic ketal ester can undergo further transesterification with another molecule of keto ester or ketal ester. Other side products can form as a result of the acid catalysis of the ketalization/acetalization and esterification/transesterification reactions where triols and higher are employed.

The cyclic ketal of levulinic acid (a keto acid) and glycerol (a triol) is disclosed in U.S. patent application Ser. No. 11/915,549, published as WO 2007/062118, the entire contents of which are incorporated herein by reference. The Application discloses a series of compounds that are based on the initial formation of the cyclic glycerol ketal of levulinic acid, 4-(2-hydroxymethyl-1,4-dioxolan-5-yl) pentanoic acid. The ketalization is carried out using between 0.7 and 1.3 molar equivalents of levulinic acid based on moles of glycerol, further in the presence of 0.0006 to 0.0033 molar equivalents of sulfuric acid based on equivalents of the limiting reagent (whether glycerol or levulinic acid).

Other examples of cyclic ketalization or acetalization reactions of polyols homogeneously catalyzed by protic acid catalysts are found in the literature. For example, F. A. J. Meskens, *Synthesis* 1981, 501-22, reviews the ketalization of 2,4-dichlorophenacyl chloride with ethylene glycol, catalyzed by p-toluenesulfonic acid monohydrate. The ketalization employs 6 molar equivalents of diol per equivalent of ketone and 0.0077 molar equivalents of catalyst per equivalent of ketone. Yield of the ketal is reported to be 72% after 66 hours reaction time. Hoover, U.S. Pat. No. 1,934,309 discloses the reaction of n-butyl aldehyde with glycerol, catalyzed by sulfuric acid. The acetalization employs a 1:1 molar ratio of triol to aldehyde and 0.0031 molar equivalents of catalyst. Yield is not reported.

Morey, U.S. Pat. No. 2,260,261 discloses the reaction of ethylene glycol, glycerol, and sorbitol with chlorinated acetones. The ketalization of ethylene glycol with 3,3-dichloroacetone is catalyzed by sulfuric acid; the reaction employs 2 molar equivalents of ketone based on diol and 0.0034 molar equivalents of catalyst based on diol, the limiting reagent (or 0.0017 molar equivalents of catalyst based on ketone). The ketalization of glycerol with 3-chlorobutanone is catalyzed by hydrochloric acid; the reaction employs 1.5 molar equivalents of ketone based on triol and 0.0300 molar equivalents of catalyst based on triol, the limiting reagent (or 0.0210 molar equivalents of catalyst based on ketone). And the ketalization of sorbitol with chloroacetone is catalyzed by sulfuric acid; the reaction employs 6.6 molar equivalents of chloroacetone based on hexyl, which corresponds to 2.2 moles of ketone per diol functionality, and 0.0172 molar equivalents of acid based on hexyl, the limiting reagent (corresponding to 0.0057 molar equivalents based on diol functionality, or 0.0026 molar equivalents based on ketone).

Bruchmann et al., U.S. Pat. No. 5,917,059 disclose the reaction of diols and triols, such as glycerol, trimethylolpropane, and ethylene glycol, with an excess of ketone, such as acetone and 2-butanone. The reaction was carried out at reflux, and removal of ketone along with water was remedied by constant addition of additional ketone during the reaction. The ketalization of four moles of ketone with one mole of diol or triol was catalyzed by 0.01 to 0.5 moles of p-toluenesulfonic acid based on moles of alcohol, the limiting reagent. Additional ketone corresponding to 8 to 15 parts by weight of ketone to one part by weight of alcohol was added during the course of the reaction. Eight to twelve hours of reaction time resulted in 97.0% to 99.5% yield of the cyclic ketal.

Other examples of ketalization or acetalization reactions of polyols homogeneously catalyzed by conventional amounts of protic acid catalysts disclose reactions with keto acids. For example, Pasto et al., *J. Am. Chem. Soc.* 87(7), 1515 (1965) disclose the ketalization of methyl 3-benzoylpropionate with ethylene glycol, catalyzed by p-toluenesulfonic acid. The reaction employs 2.6 molar equivalents of diol based on keto acid and 0.076 molar equivalents of catalyst based on keto acid. Yield is not reported. Ono et al., *J. Am. Oil Chem. Soc.* 70(1), 29 (1993) disclose ketalization of ethyl pyruvate, ethyl acetoacetate, and ethyl levulinate with various 1-O-alkyl glycerols (diols). The reaction is catalyzed by p-toluenesulfonic acid and employs 1.2 molar equivalents of diol based on moles of keto ester and 0.0500 molar equivalents of catalyst based on moles of ketal ester. Yield is reported to be 96% after two hours of reaction time. McCullough et al., U.S. Pat. No. 5,998,092 disclose the ketalization of two keto acids with ethylene glycol, catalyzed by p-toluenesulfonic acid. The reaction of ethyl 2-(4-vinylbenzyl)-3-oxo-butanoate and ethylene glycol employs 2 molar equivalents of ethylene glycol based on keto ester and 0.0150 molar equivalents of catalyst based on keto ester. Yield is reported to be 81% after 72 hours of reaction time. The reaction of ethyl 2-acetyl-5-hexanoate and ethylene glycol employs 2 molar equivalents of ethylene glycol based on keto ester and 0.0100 molar equivalents of catalyst based on keto ester. Yield is reported to be 81% after 48 hours of reaction time.

Homogeneous acid catalyzed esterification also employs protic acid catalysts, typically in the same range of concentration as the above acetalization and ketalization reactions. For example, ATOFINA Publication No. A-70-1 (© 2001 by Atofina Chemicals, Inc. of Philadelphia, Pa.; available on the internet at http://staging.arkemainc.com/literature/pdf/405.pdf) discloses the esterification of phthalic anhydride with 2-ethylhexanol, employing protic catalysts at various levels. In each case, 2 molar equivalents of alcohol based on phthalic anhydride are employed. Methanesulfonic acid is employed as the catalyst at between 0.0051 and 0.0146 molar equivalents based on alcohol (twice that based on anhydride). Sulfuric acid is employed as the catalyst at between 0.0072 and 0.0143 molar equivalents based on alcohol (twice that based on anhydride). And p-toluenesulfonic acid is employed as the catalyst at between 0.0038 and 0.0074 molar equivalents based on alcohol (twice that based on anhydride). Yields of esterified product ranged from approximately 75% to 97.5% after five hours reaction time. Otera, *Esterification, p. 9* (© 2003 Wiley-VCH Verlag GmbH & Co.) discloses a generic esterification procedure for an unspecified carboxylic acid with t-butanol catalyzed by sulfuric acid. The reaction employs 5 molar equivalents of alcohol based on the carboxylic acid and 1 molar equivalent of sulfuric acid based on the carboxylic acid. Yield is not reported. A technical bulletin available from E.I. du Pont de Nemours and Company of Wilmington, Del., "DuPont™ TYZOR® Organic Titanates Technical Note-Direct Esterification" (© 2001 by E.I. du Pont de Nemours and Company) outlines a procedure for esterification of adipic acid with two equivalents of 2-ethylhexyl alcohol catalyzed by sulfuric acid. The reaction employs 0.0089 molar equivalents of catalyst based on adipic acid. Yield is reported to be 100% after 90 minutes reaction time.

While the above references are not exhaustive, they are exemplary in terms of the stoichiometries of reagents employed as well as the amounts and types of acid catalysts used for ketal and acetal formation. The references show that the types and amounts of acid catalysts used for acetalization and ketalization are the same as those employed in esterification reactions. This translates to selectivity issues in selectively forming ketals or acetals in the case of keto acids, semialdehydes, or esters thereof, because esterification or transesterification reactions readily compete with ketalization or acetalization reactions due to the dual functionality of the keto acids and semialdehydes. Particularly where triols and higher polyols are employed in such reactions, side products can form due to the multiple hydroxyl functionality of the polyols and the presence of carboxylic functionality in the keto acid, semialdehyde, or ester thereof as well as the corresponding ketal or acetal product.

When reacting alcohols with keto acids, semialdehydes, and esters thereof, it is desirable to provide selectivity of ketal or acetal formation over esterification or transesterification reactions. It is desirable to reduce the overall concentration of the side products when forming a ketal or acetal of a keto acid, semialdehyde, or ester thereof. It is desirable to reduce the total number of side product species when forming a ketal or acetal of a keto acid, semialdehyde, or ester thereof. It is desirable to accomplish these goals while still retaining the fast reaction rate of ketal or acetal formation afforded by the use of an acid catalyst. It is desirable to employ a reaction methodology that produces high yields of ketal and acetal. It is desirable to employ a reaction methodology that is simple and cost effective.

SUMMARY OF THE INVENTION

We have found that in the formation ketals or acetals of keto acids, semialdehydes, or esters thereof with alcohols, use of an acid catalyst at a level that at least an order of magnitude lower than the conventional concentrations of acid catalysts employed relative to the limiting reagent results in an unexpectedly selective reaction producing high yields of the desired ketal or acetal of high purity in conjunction with fast reaction rates. Further, by employing the method of the invention, the rate of ketal or acetal formation is commensurate with, or even faster than, the rate of ketal or acetal formation traditionally observed in acid catalyzed reactions employing conventional concentrations of acid catalyst, without the concomitant formation of significant amounts of trans-esterified side-products typically observed when traditional amounts of acid catalyst are employed.

We have also discovered that a reaction employing at least a 2.5 molar excess of keto acid, semialdehyde, or ester thereof relative to moles of a polyol capable of forming a cyclic ketal results in a higher ratio of ketal or acetal to esterified or transesterified products than the same reaction employing standard stoichiometry and amount of acid catalyst.

When the low level of acid catalyst is combined with the use of at least a 2.5 molar excess of the keto acid, semialdehyde, or ester thereof relative to alcohol or polyol, yet another surprising result is observed: the ketal or acetal formation was accomplished with even less side product formation, and with even faster reaction rates. Thus, a reaction employing a very low level of acid and a significant excess of keto acid, semialdehyde, or ester thereof results in very high yields of ketal or acetal while providing a surprisingly high rate of reaction. Yields of the desired product are, in embodiments, above 95%, while transesterification products are 5% or less; reaction times are less than 24 hours.

An additional advantage of using the low acid methods of the invention includes the obviation of the need to neutralize the reaction product. An additional advantage of employing an excess of keto acid, semialdehyde, or ester thereof is the utility of the excess keto acid, semialdehyde, or ester thereof in forming an azeotrope with the water generated by the ketalization or acetalization reaction. An additional feature of the method of the invention is the miscibility imparted by retaining some amount of the ketal or acetal reaction product in the reaction vessel, thereby obviating the need for cosolvents or additional surfactants and providing for a solventless reaction system. The methods of the invention also provide for ease of implementation of a wide variety of processing techniques.

Additional advantages and novel features of the invention will be set forth in part in the description that follows, and in part will become apparent to those skilled in the art upon examination of the following, or may be learned through routine experimentation upon practice of the invention.

DETAILED DESCRIPTION

Figure 1:
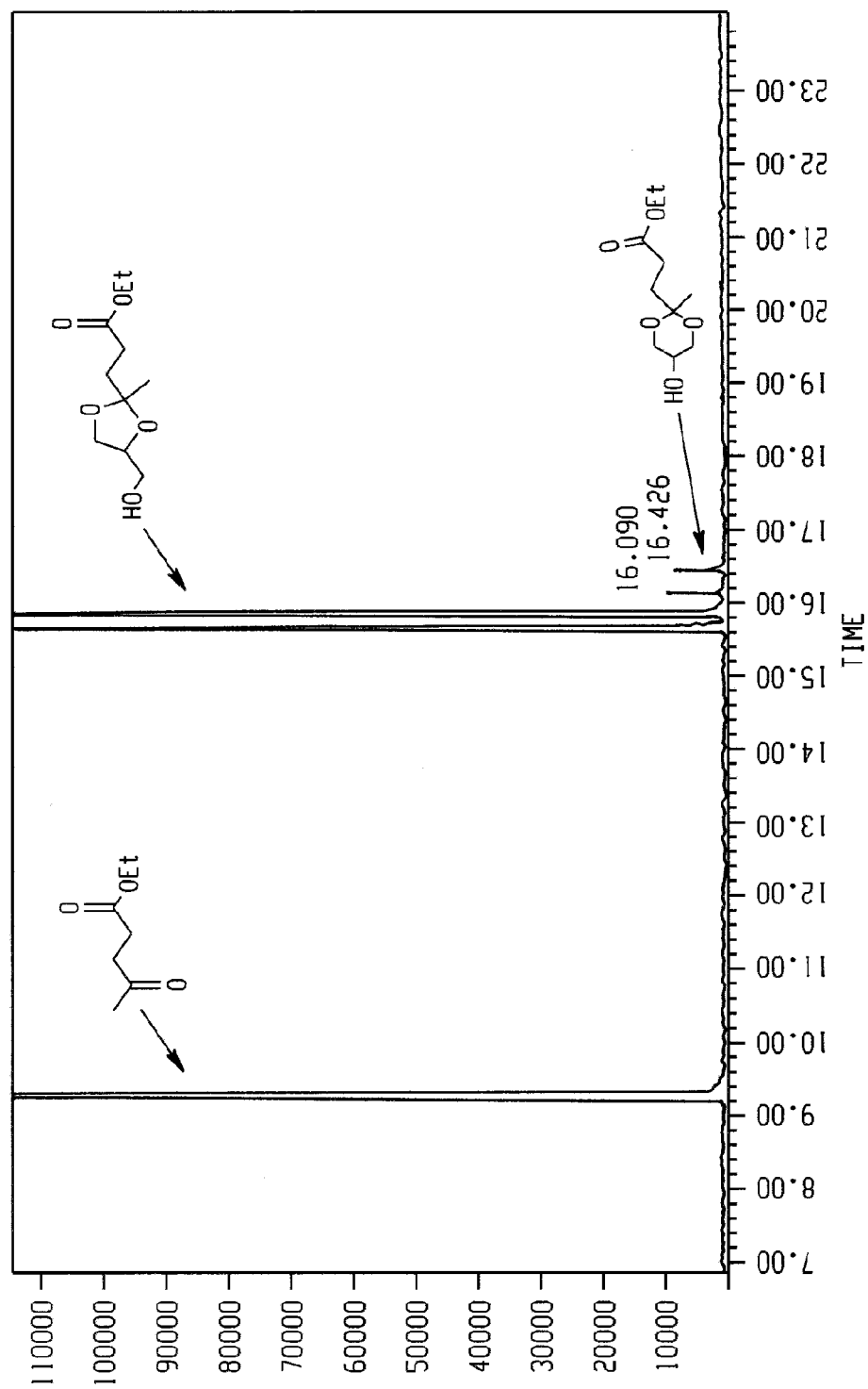
FIG. 1 is the GC portion of a GC-MS of the reaction mixture at the end of the reaction corresponding to Example 2.

Various embodiments of the invention will be described in detail. Reference to various embodiments does not limit the scope of the claims attached hereto. Additionally, any examples set forth in this specification are not intended to be limiting and merely set forth some of the many possible embodiments for the appended claims.

The compounds made by the method of the invention have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

A method of the invention encompasses the formation of ketal or acetal adducts of keto acids, semialdehydes, or esters thereof with alcohols. These reactions are depicted as Reaction I and Reaction II below:

Reaction I

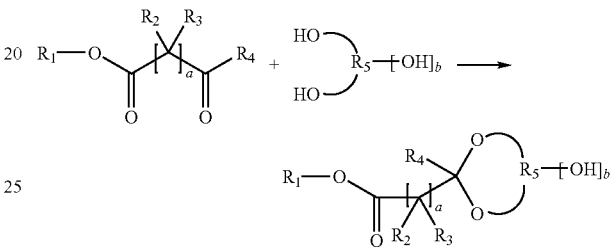

Reaction II

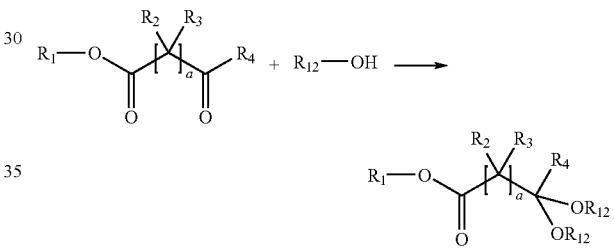

wherein $R_1$, $R_2$, $R_3$, and $R_4$ are independently hydrogen, a linear alkyl group, a branched alkyl group, a cyclic alkyl group, a linear alkenyl group, a branched alkenyl group, a cyclic alkenyl group or alkenyl group, an aryl group, or alkaryl group having 1 to 18 carbon atoms. $R_{12}$ is a linear alkyl group, a branched alkyl group, a cyclic alkyl group, a linear alkenyl group, a branched alkenyl group, a cyclic alkenyl group or alkenyl group, an aryl group, or alkaryl group having 1 to 18 carbon atoms; and a is 0 or an integer of 1 to 12.

Any of $R_1$, $R_2$, $R_3$, $R_4$, and $R_{12}$ also contain, in embodiments one or more heteroatoms. Without limiting the species of heteroatoms that might be present in one or more embodiments, heteroatoms can include one or more of oxygen, nitrogen, halogen atoms such as chlorine or bromine, sulfur, silicon, or phosphorus. The heteroatoms are present, in embodiments, as one or more functional groups such as, for example, carbonate, carboxylic acid, carboxylic ester, sulfone, imide, amide, amine, mercapto, ether, disulfide, phosphate, phosphonooxy, siloxane, silyl, or silane functionalities and are not particularly limited in their compositions except that the one or more additional functional groups do not include hydroxyl or thiol functionality unless the hydroxyl or thiol functionality is protected by a protecting group.

$R_5$ is a group derived from a diol or higher polyol that can be a polymeric polyol such as poly(vinyl alcohol), an hydroxyl functionalized surface such as silica, a silane, siloxane, or silanol group, or a hydrocarbon group having the formula

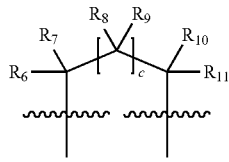

wherein c is 0 or 1 and $R_6$, $R_7$, $R_8$, $R_9$, $R_{10}$, and $R_{11}$ are independently hydrogen, linear alkyl, branched alkyl, cyclic alkyl, linear alkenyl, branched alkenyl, cyclic alkenyl, aryl, or alkaryl. Any of $R_6$, $R_7$, $R_8$, $R_9$, $R_{10}$, and $R_{11}$ can contain, in embodiments, one or more heteroatoms; b is 0 or an integer; and c is either 0 or 1.

The method of the invention results, in embodiments, in compounds having one or more isomers. Where an isomer can exist, it should be understood that the method of the invention contemplates all isomers thereof that can arise, including stereoisomers, conformational isomers, and cis, trans isomers; isolated isomers thereof; and mixtures thereof.

The amount of acid catalyst employed in the method of the invention is, in embodiments, about $1\times10^{-6}$ to $1\times10^{-3}$ moles of acid catalyst per mole of limiting reagent. In such embodiments, the limiting reagent is the alcohol. In other embodiments, about $1\times10^{-6}$ to $1\times10^{-4}$ moles of catalyst per mole of limiting reagent is used. In still other embodiments, about $1\times10^{-6}$ to $1\times10^{-5}$ moles of catalyst per mole of limiting reagent is used. The limiting reagent is, in embodiments, a monofunctional alcohol, diol or higher polyol; in other embodiments, the limiting reagent is the ketal acid, semialdehyde, or ester thereof. In some embodiments where the alcohol is a diol or higher polyol capable of forming a cyclic ketal, a molar ratio of about 1.05 moles or greater of keto acid, semialdehyde, or ester thereof per mole of alcohol is used. In still other embodiments where the alcohol is a diol or higher polyol capable of forming a cyclic ketal, a molar ratio of about 2.50 moles or greater of keto acid, semialdehyde, or ester thereof per mole of alcohol is used. In other embodiments, about 3.50 moles or greater of keto acid, semialdehyde, or ester thereof per mole of alcohol is used. In still other embodiments, about 4.50 moles or greater of keto acid, semialdehyde, or ester thereof per mole of alcohol is used in the method of the invention. Where at least 2.5 moles or greater of keto acid, semialdehyde, or ester thereof per mole of a diol or higher polyol capable of forming a cyclic ketal is employed, the amount of acid catalyst is, in embodiments, commensurate with conventional concentrations of acid catalyst. In such embodiments, significantly less transesterification is observed compared to traditional stoichiometries employed.

In carrying out Reaction I or Reaction II, the method of the invention effectively reduces the amounts of esterified side products and thus improves yield and purity of the products. Reactions Ia, Ib, Ic, and IIa, below, represent some of the side reactions of Reaction I and Reaction II, respectively, that can occur using conventional methods employed in the literature. These side reactions are, in embodiments, minimized or even completely suppressed by employing the method of the invention. Reaction Ia shows one possible mode of reaction; reaction at other hydroxyl sites are also contemplated. Reactions Ib and Ic can occur where a triol is employed (b≥1). Where b≥2, additional side reactions can occur that are not shown below.

Reaction Ia

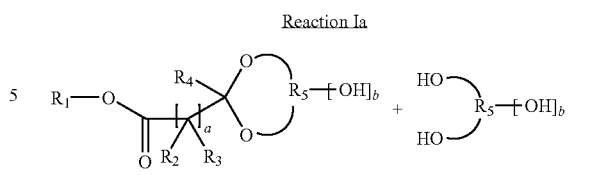

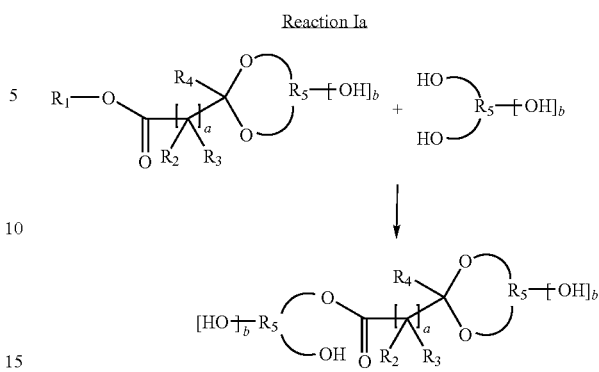

Reaction Ib

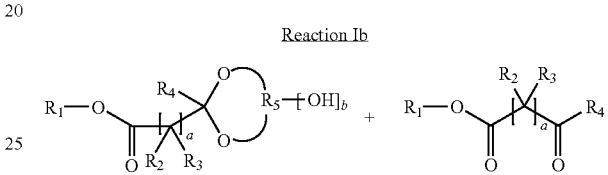

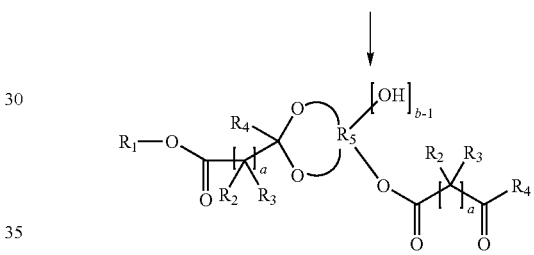

Reaction Ic

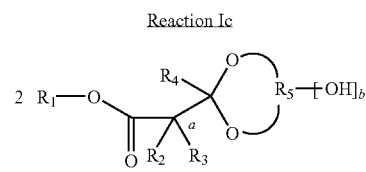

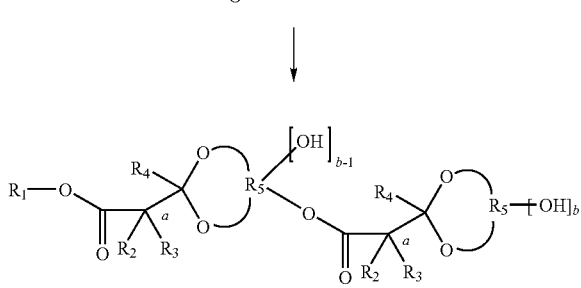

Reaction IIa

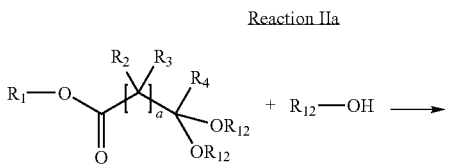

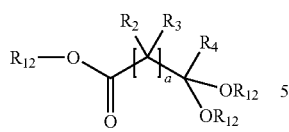

In embodiments, the cyclic ketal or cyclic acetal products of one mole of a diol, triol, or higher polyol with one mole of keto acid, semialdehyde, or ester thereof as shown in Reaction I are generally referred to as "1:1 adducts." Thus, 1:1 adducts are, in embodiments, cyclic ketal acids, cyclic ketal esters, cyclic acetal acids, or cyclic acetal esters. The polyols used to make cyclic ketals or acetals in such embodiments may be linear, branched, cyclic, or polymeric; the polyol may comprise additional chemical moieties and/or heteroatoms in addition to having at least two hydroxyl moieties capable of cyclic ketal or acetal formation.

In other embodiments, monofunctional linear, branched, cyclic, aryl, aralkyl, or polymeric compounds with one hydroxyl moiety, or polyols wherein hydroxyl moieties are disposed in such a way that a cyclic ketal or acetal cannot form, ketals and acetals of keto acids, semialdehydes, or esters thereof are selectively formed by employing the method of the invention. In such embodiments, two moles of alcohol react with one mole of keto acid, semialdehyde, or an ester thereof to form the ketal or acetal product, as shown in Reaction II. Such embodiments are generally referred to as "2:1 adducts." Thus, 2:1 adducts are, in embodiments, ketal acids, ketal esters, acetal acids, or acetal esters of alcohols such that the ketal or acetal moiety is not cyclic. The alcohols employed in such embodiments may have additional functional moieties and/or heteroatoms in addition to having at least one hydroxyl moiety capable of cyclic ketal or acetal formation.

The invention encompasses a method of forming 1:1 adducts and 2:1 adducts employing about $1\times10^{-6}$ to $1\times10^{-3}$ molar equivalents of acid catalyst per mole of limiting reagent. The limiting reagent is, in embodiments, a monofunctional alcohol, diol or higher polyol; in other embodiments, the limiting reagent is the ketal acid, semialdehyde, or ester thereof.

In our previous studies and as disclosed in U.S. patent application Ser. No. 11/915,549, 0.7 to 1.3 molar equivalents of levulinic acid based on moles of glycerol (a 1,2,3 triol that is capable of forming a cyclic ketal), further in the presence of 0.0006 to 0.0033 molar equivalents of sulfuric acid based on the limiting reagent, was employed to give the 1:1 adduct. The stoichiometry and amount and type of acid catalyst employed corresponds to both conventional ketalization and esterification techniques. The desired reaction forming the glycerol ketal of levulinic acid, designated as compound 1, is shown below.

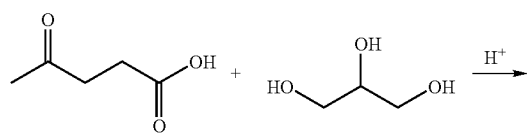

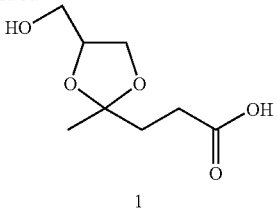

Due to multiple reactive sites, however, many different side products can form in the presence of sulfuric acid. For example, where the desired product is the 1:1 adduct of glycerol and levulinic acid or an ester thereof, commonly observed and identified side products of Reaction I wherein the above include compounds 2-5 below, wherein $R_1$ is as defined above.

We have found that by employing the method of the invention, an unexpected and counterintuitive reduction in side products such as structures 2, 3, and 4 is observed while the reaction rate to form the desired 1:1 adduct is undiminished and, in embodiments, even accelerated compared to previously reported reaction protocols. Thus, selectivity is increased for ketal formation at levels of $1\times10^{-6}$ to $1\times10^{-3}$ moles of acid catalyst relative to moles of the limiting reagent, when compared to the same reactions employing traditional levels of acid catalysts. In yet another unexpected finding, this effect is increased by providing a molar excess of the keto acid, semialdehyde, or ester thereof relative to the amount of alcohol employed in the reaction. This is a surprising result because it would be expected that providing a molar excess of e.g. keto ester in such a reaction would increase the concentration of the reaction product arising from the transesterification reaction of alcohol with the ester functionality of the keto ester.

This unexpected result applies to the general reaction scheme of alcohols with keto acids, semialdehydes, or esters thereof where the desired product of the reaction is the 1:1 adduct or 2:1 adduct. The method of the invention results in a higher yield of the desired ketal or acetal with minimization of side reactions than similar reactions run with standard acid levels, stoichiometries approaching 1:1, or both. Thus, in embodiments where both ketal/acetal formation as well as transesterification can take place, using the above ratios of reagents, molar equivalents of acid catalyst, or both, improves selectivity for the 1:1 or 2:1 adduct.

We have also found that by employing the method of the invention, the rate of ketal or acetal formation is about the same as, or even faster than, the rates of reaction observed for traditional acid catalyst levels and stoichiometry. This is also surprising, as the apparent rate of formation of other reaction products is apparently reduced. Thus, the method of the invention provides selective ketalization/acetalization where the ketalization/acetalization reaction competes with esterification/transesterification reactions.

"Keto acid" refers to a compound having at least one ketone moiety and one carboxylic acid moiety. A compound may have more than one ketone functionality or more than one carboxylic acid functionality. The keto acid is not particularly limited as to additional moieties or functionalities present in addition to the ketone and carboxylic acid functionalities. In some embodiments, the compound may also contain one or more halogen, carbonate, carboxylic acid, carboxylic ester, sulfone, imide, amide, amine, mercapto, protected thiol, protected hydroxyl, ether, disulfide, phosphate, phosphonooxy, siloxane, silyl, or silane functionalities. Some examples of suitable keto acids include pyruvic acid, acetoacetic acid, levulinic acid, 5-aminolevulinic acid, oxaloacetic acid, α-ketobutyric acid, α-ketoglutaric acid, α-ketoisovaleric acid, 5-ketohexanoic acid, α-ketoisocaproic acid, α-ketoadipic acid, 3-ketoadipic acid, 2-keto-4-methylthiobutyric acid, 4-acetylbutyric acid, 2-keto-3-bromobutyric acid, phenylpyruvic acid, 2-keto-3-phenylpropanoic acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, 13-keto-9,11-octadecadienoic acid, 4-ketostearic acid, 9-ketopalmitic acid, 4-ketoheptanedioic acid, penicillic acid, 8-keto-8-aminopelargonic acid, 2-keto-5-aminovaleric acid, 2-succinylamino-6-oxoheptanedioic acid, 2-oxo-3-butynoate, 3-keto-6-acetamidohexanoate, and the like. Additionally, a keto acid may contain hydroxyl or mercapto functionality provided it is protected, e.g. by one or more trimethylsilyl or t-butyl groups, or one or more other protecting groups known to those of skill in the art.

In embodiments of the invention, the keto acid employed is levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. Other keto acids and keto esters include pyruvic acid and esters thereof, and acetoacetic acid and esters thereof. Esters of levulinic acid are also employed in embodiments of the invention, for example, ethyl levulinate and n-butyl levulinate.

"Keto ester" refers to the carboxylic ester of the one or more carboxylate functionalities of any of the above described keto acid compounds. Thus, in Reaction I above, the $R_1$ group in a keto ester is not hydrogen. The $R_1$ group is, in embodiments, a linear, branched, or cyclic alkyl or alkenyl group having 1 to 18 carbon atoms, or an aryl or alkaryl group, wherein the alkyl, alkenyl, aryl, or alkaryl groups can have one or more additional functional groups that can include, for example, halogen, carbonate, amide, amine, mercapto, ether, or silane functionalities. Thus, $R_1$ can be, in embodiments, methyl or ethyl; a linear or branched isomer of an alkyl group such as propyl, butyl, pentyl, hexyl, septyl, octyl, nonyl, decyl, undecyl, dodecyl, tetradecyl, cetyl, or stearyl; a cycloalkyl group such as cyclohexyl, cyclooctyl, norbornyl, and the like; an alkynyl group such as ethynyl, 3-methylpent-1-yn-3-yl, tetradec-9-yn-1-yl, and the like; an aryl and alkaryl group such as phenyl, benzyl, tolyl, xylyl, 5-phenylpent-1-yl, and the like; wherein the alkyl, alkenyl, alkynyl, aryl, or alkaryl may additionally have one or more functional groups, for example, 1,1,1-trichloro-2-methyl-2-propyl, 5-fluoro-1-pentyl, 5-amino-1-pentyl, 5-benzyloxy-1-pentyl, 5-methoxy-1-pentyl, 3-nitro-2-pentyl, 4-methylthio-1-butyl, 1-carboxyhex-6-yl, propionamid-2-yl, and the like. $R_1$ can also be a protecting group, such as trimethylsilyl, phosphonooxy, or a phosphatidyl group. The composition of the $R_1$ group is not particularly limited; however, if there are hydroxyl or thiol functionalities present on the $R_1$ group they should further be protected by a protecting group, such as trimethylsilyl, t-butyl, phosphonooxy, benzyl, tetrahydropyranyl, or another group generally known in the art to be a protecting group, to avoid side reactions of the free hydroxyl or thiol with a neighboring oxo group.

In some embodiments of the invention, ethyl levulinate or n-butyl levulinate is employed as the keto ester. These esters are based on levulinic acid, an abundant feedstock that is prepared on an industrial scale by acidic degradation of hexoses and hexose-containing polysaccharides such as cellulose, starch, sucrose, and the like.

"Semialdehyde" refers to a compound having at least one aldehyde functionality and one carboxylic acid functionality. A compound may have more than one aldehyde functionality or more than one carboxylic acid functionality. The semialdehyde is not particularly limited as to additional moieties or functionalities present in addition to the aldehyde and carboxylic acid functionalities. In some embodiments, the compound may also contain one or more halogen, carbonate, carboxylic acid, carboxylic ester, sulfone, imide, amide, amine, mercapto, protected thiol, protected hydroxyl, ether, disulfide, phosphate, phosphonooxy, siloxane, silyl, or silane functionalities. Some examples of suitable semialdehydes include aspartic semialdehyde, 4-oxobutanoic acid, 5-oxopentanoic acid, 6-oxohexanoic acid, 7-oxoheptanoic acid, α-formylglycine, 3-oxo-2-(phosphonooxy)-propanoic acid (tartronic semialdehyde wherein the hydroxyl group is protected by phosphate), 3-oxopropanoic acid (malonic semialdehyde), 2-methyl-3-oxopropanoic acid (methylmalonic semialdehyde), succinic semialdehyde, adipic semialdehyde, 5-glutamyl semialdehyde, allysine, 2-aminomuconic semialdehyde, 4-amino-5-oxopentanoic acid, N-acetylglutamic semialdehyde, 2-amino-3-(3-oxoprop-1-enyl)-but-2-enedioic acid, and N2-succinyl-L-glutamic-5-semialdehyde. Many other semialdehydes are available by carrying out ozonolysis of unsaturated fatty acid esters to form an aldehyde moiety at an unsaturated site, as described by Criegee, *Angew. Chem. Int. Ed.*, 1975, 87, 745.

"Semialdehyde ester" refers to the carboxylic ester of the one or more carboxylate functionalities of any of the above described semialdehyde compounds. The nature of the ester group is generally the same as those described above for the keto ester functionalities. The composition of the ester $R_1$ group, as shown in Reaction I, is not particularly limited; however, if there are hydroxyl or thiol functionalities present on the $R_1$ group they should further be protected by a protecting group, such as a trimethylsilyl group or another group generally known in the art to be a protecting group, to avoid side reactions of the free hydroxyl or thiol with a neighboring oxo group.

"Alcohol" or "monofunctional alcohol" refers to an hydroxyl functionalized linear, branched, or cyclic alkyl, alkenyl, or alkynyl group having 1 to 18 carbon atoms to 1 to 6 carbon atoms, or an aryl or alkaryl group, wherein the alkyl, alkenyl, alkynyl, aryl, or alkaryl groups may have one or more additional functionalities that may include, for example, halogen, carbonate, carboxylic acid, carboxylic ester, sulfone, imide, amide, amine, mercapto, thiol, protected hydroxyl, ether, disulfide, phosphate, phosphonooxy, siloxane, silyl, or silane functionalities. Examples of suitable monofunctional alcohols include methanol; ethanol; various linear and branched isomers of propanol, butanol, pentanol, hexanol, octanol, nonanol, decanol, undecanol, dodecanol, tetradecanol, cetyl alcohol, and stearyl alcohol; cycloalkyl alcohols such as cyclohexanol, cyclooctanol, norbornyl alcohol, and the like; alkynyl alcohols such as ethynyl alcohol, 3-methylpent-1-yn-3-ol, tetradec-9-ynol, and the like; aryl and alkaryl alcohols such as phenol, benzyl alcohol, toluol, xylyl alcohol, 5-phenylpentanol, and the like; and alcohols having various functional groups, for example 1,1,1-trichloro-2-methyl-2-propanol, 5-fluoro-1-pentanol, 5-amino-1-pentanol, 5-benzyloxy-1-pentanol, 5-methoxy-1-pentanol, 3-nitro-2-pentanol, 4-methylthio-1-butanol, 6-hydroxyhexanoic acid, lactamide, and the like.

"Polyol" refers to a compound containing two or more hydroxyl groups. In embodiments, the polyol is a polymeric polyol such as poly(vinyl alcohol). In other embodiments the polyol is an hydroxyl functionalized surface such as silica. In other embodiments the polyol is a silane, siloxane, or silanol group. In other embodiments, the polyol is a hydrocarbon based compound with one or more alkynyl groups or linear, branched, or cyclic alkyl or alkenyl groups having 1 to 18 carbon atoms, or aryl or alkaryl groups. In embodiments, the alkyl, alkenyl, aryl, or alkaryl groups can have one or more additional functional groups that can include, for example, halogen, sulfone, imide, amide, mercapto, ether, disulfide, phosphate, phosphonooxy, siloxane, silyl, or silane, or a protected hydroxyl or thiol.

In some embodiments, the method of the invention employs polyols wherein at least two of the hydroxyl groups are either on adjacent carbon atoms or have one carbon atom spaced between hydroxyl-bearing carbons. These conformations are shown as (a) and (b) below, respectively, wherein the dashed lines indicate that other moieties attached to the carbon atoms are not limited. Such compounds are capable of forming dioxolanes and dioxanes, respectively, when reacted with compounds bearing carbonyl moieties.

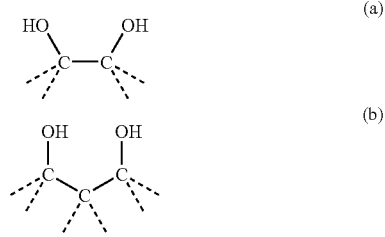

The polyols have, in embodiments, the Examples of polyols suitable for forming cyclic ketals from oxo moieties include 1,2-ethanediol (ethylene glycol), 1,2-propanediol (propylene glycol), 1,3-propanediol, 1,2,3-propanetriol (glycerol), diglycerol (a mixture of glycerol dimers coupled at primary and secondary hydroxyl moieties), 2,2-dimethyl-1,3-propanediol (neopentyl glycol), 3-mercaptopropane-1,2-diol (thioglycerol), dithiothreitol, 1,1,1-trimethylolpropane, 1,2-butanediol, 1,3-butanediol, pentaerythritol, cyclohexane-1,2-diol, 1,4-dioxane-2,3-diol, 1,2,3-butanetriol, 1,3,4-butanetriol, 1,2,3-heptanetriol, 4-menthane-1,7,8-triol, 3-butene-1,2-diol, benzene-1,2-diol (catechol), 3-chlorocatechol, indane-1,2-diol, tartaric acid, and 2,3-dihydroxyisovaleric acid; and pentose and hexose sugars including mannitol, sorbitol, xylitol, threitol, erythrol, erythritol, maltitol, lactitol, raffinose, and stachyose; pentaerythritol derivatives and other polyhydric alcohol derivatives such those sold under the trade name CHARMOR® by Perstorp Polyols, Inc. of Toledo, Ohio; and poly(vinyl alcohol) and copolymers thereof, such as MOWITAL™ resin available from the Kuraray Company of Osaka, Japan, and AQUASOL™ resin available from A. Schulman, Inc. of Akron, Ohio, or ELVANOL® resin available from the DuPont Company of Wilmington, Del.

In some embodiments, polyols that do not form cyclic ketals with keto acids, semialdehydes, or esters thereof are employed. Such polyols react, in embodiments of the invention, as monofunctional alcohols such that two moles of polyol react to produce acetal or ketal functionality. These polyols will subsequently have at least one residual hydroxyl group available for additional ketalization/acetalization or esterification/transesterification reactions. Examples of polyols that, in embodiments, do not form cyclic ketals or acetals include 1,4-butenediol, diethylene glycol, 2,3-dibromobutene-1,4-diol, xylene glycol, 1,3-benzenediol (resorcinol), 1,4-benzenediol (hydroquinone), 2-butyne-1,4-diol, 3-hexyne-3,5-diol (SURFYNOL® 82, available from Air Products of Allentown, Pa.) and other alkyne-based polyol products marketed under the SURFYNOL® brand name by Air Products of Allentown, Pa.

Polymeric diols and polyols aside from polyvinyl alcohol and copolymers thereof are also useful in embodiments of reactions employing the methods of the invention. Suitable polymeric diols and polyols include, in embodiments, polyether polyols based on ethylene glycol, such as CARBOWAX® polyethylene glycols, available from Dow® Company of Midland, Mich.; oligomeric and polyether diols and polyols based on propylene glycol or combinations of ethylene glycol and propylene glycol, such as those sold by the Dow® Company of Midland, Mich., and polyether glycols such as those produced by the INVISTA™ Company of Wichita, Kans. under the trade name TERETHANE®; dendritic polyols, for example those sold under the trade name BOLTORN® by Perstorp Polyols, Inc. of Toledo, Ohio; polycarbonatediols of varying molecular weights, such as L467 m, L600 m, and L565 m, available from Asahi Kasei Corporation (Tokyo, Japan); polyols based on hydroxylated vegetable oils, such as those sold under the trade name BiOH®, available from the Cargill Company of Wayzata, Minn.; hydroxyl-terminated polybutadienes, such as HTPB R45M, sold by Aerocon Systems of San Jose, Calif. Other useful polymeric polyols include those produced by the Everchem Company of Media, Pa., or the Maskimi Polyol Sdn. Bhd. of Kajang, Selango Darul Ehsan, Malaysia and the polyols employed in the Union Carbide Company (South Charleston, W. Va.) publication by Carey, M. A. et al., "Rapid Method for Measuring the Hydroxyl Content of Polyurethane Polyols" (published on the internet at http://www.polyurethane.org/s_api/doc_paper.asp?CID=1044&DID=4060).

It should be understood that in the case of polymeric polyols not configured with one or more pairs of hydroxyls in the 1,2 or 1,3 position on a polymer chain, it is statistically possible to form a cyclic ketal by an intramolecular reaction of two hydroxyl groups present on the polymeric polyol with a keto acid, semialdehyde, or an ester thereof. However, the main product of such reactions is not, in embodiments, the result of such an intramolecular reaction of the polyol.

In some embodiments, the polyol employed in the reaction is glycerol. Glycerol is an inexpensive renewable compound that is readily available as a by-product of biodiesel production or via fermentation of carbohydrates. Since glycerol forms the backbone of triglycerides, it is produced upon saponification or transesterification of these compounds. Soap-making and biodiesel production are respective examples. Glycerol is a roughly 10% by-product of biodiesel manufacture, via transesterification of vegetable oils.

The term "acid" or "acid catalyst" refers generally to either Lewis or Brønsted-Lowry acids. In embodiments, acid catalysts that are known homogeneous catalysts for either ketal or acetal formation or esterification or transesterification reactions are suitable acid catalysts for use with the method of the invention. The method of the invention is not particularly limited as to the particular species of acid catalyst employed. In embodiments, the acid catalysts employed in the method of the invention are strong protic acid catalysts. Strong protic acids (Brønsted-Lowry acids) are those that have a $K_a$ of 55 or greater. Examples of suitable strong protic acid catalysts include sulfuric acid, arylsulfonic acids and hydrates thereof, such as p-toluenesulfonic acid monohydrate, perchloric acid, hydrobromic acid, and hydrochloric acid. In other embodiments, the acid catalysts employed in the method of the invention are weak protic acid catalysts. Weak protic acid catalysts are those having a $K_a$ of less than 55. Examples of suitable weak protic acid catalysts include phosphoric acid or orthophosphoric acid, polyphosphoric acid, and sulfamic acid. In other embodiments, the acid catalysts employed in the method of the invention are aprotic, i.e. non-Brønsted-Lowry acids. Such acids are sometimes referred to as Lewis Acids. Such acid catalysts can include, for example, titanium tetrachloride, aluminum trichloride, and boron trifluoride. In some embodiments, more than one type of acid catalyst is used; thus, blends of one or more of the acids mentioned above may be used in a mixture to catalyze the reactions according to the method of the invention.

In some embodiments, the acid catalyst is incorporated into, or onto, or covalently bound to, a solid support material. Resin beads, membranes, porous carbon particles, zeolite materials, and other solid support materials may be functionalized with acid moieties that are, in embodiments, covalently bound or strongly sorbed to one or more surfaces of the solid support. In a nonlimiting example, sulfonated resin is used in embodiments of the invention, which provide active sulfonic acid groups that are covalently bonded to the resin.

In embodiments, reactions employing the method of the invention may be carried out in the absence of catalyst. In some embodiments, the ketalization or acetalization reaction in the absence of acid catalyst is considerably slower, and higher temperatures may be required to achieve significant levels of conversion. However, when the ketalization or acetalization reaction is carried out in the absence of acid catalyst, the resulting product is substantially acid free and thus useful for direct subsequent polymerizations, transesterifications, or other reactions that employ catalysts sensitive to the presence of an acid. Non-limiting examples of acid sensitive catalysts include titanium alkoxides, alkyl tin alkoxides such as dibutyltin methoxide, or other metal alkoxides, alkyl metal acetylates such as dibutyltin diacetate and dibutyltin dilaurate, metal hydroxides, metal oxides, metal triflates, or halogenated metals such as boron trifluoride or aluminum trichloride.

In some embodiments, the method of the invention obviates the need to neutralize acid after the reaction is complete. It is known in the art that acid catalysts can be readily neutralized with various organic or inorganic bases. However, it is in embodiments, difficult and impractical to achieve a satisfactory and reproducible neutralization of reaction mixtures comprising the ketals or acetals of keto acids, semialdehydes, and esters thereof in the presence of conventional amounts of acids such as are typically used to catalyze ketalization/acetalization or esterification/transesterification. The method of the present invention is therefore advantageous for industrial practice as the reaction product mixture comprising the desired ketal or acetal can be directly subjected to distillation without encountering significant undesired by-product, tar or polymer formation. In other embodiments, yield of the distilled 1:1 adduct or 2:1 adduct may be increased by neutralization of the acid catalyst prior to distillation. In these embodiments, the acid catalyst may be neutralized by addition to the reaction mixture of one or more metal oxides, metal hydroxides, or metal carbonates. Nonlimiting examples of such materials include magnesium oxide, sodium hydroxide, or sodium carbonate.

In some embodiments, the method of the invention employs a substantially nonvolatile acid catalyst such that the acid does not transfer into the distillate. For example, sulfuric and sulfamic acid may be employed in such embodiments. In other embodiments, resin based acid catalysts are used. Many commercially available resin based acid catalysts are sold as ion exchange resins. One type of useful ion exchange resin is a sulfonated polystyrene/divinyl benzene resin, which supplies active sulfonic acid moieties for catalyzing the reactions of the invention. Useful commercial ion exchange resins include LEWATIT® ion exchange resins sold by the Lanxess Company of Pittsburgh, Pa.; DOWEX™ ion exchange resins sold by the Dow Company of Midland, Mich.; and AMBERLITE® and AMBERLYST® ion exchange resins sold by the Rohm and Haas Company of Philadelphia, Pa. In embodiments, AMBERLYST® 15 is employed in reactions embodying the method of the invention. In these embodiments, the resin based catalyst is washed with an alcohol, such as methanol or ethanol, and then dried prior to use. In embodiments, these resins are added to a reaction mixture, providing a nonvolatile source of acid protons for catalyzing the reactions using the method of the invention. In some embodiments, these catalysts are packed into columns and the reactions carried out therein. As the reagents elute through the column, the reaction is catalyzed and the eluted products are free of acid. In other embodiments, the ion exchange resin is slurried in a pot containing the reagents, the reaction is carried out, and the resulting reaction products filtered or distilled directly from the resin, leaving an acid-free material.

In embodiments, the reaction is carried out under elevated temperatures, for example at temperatures in the range between about 60° C. and 200° C., typically between about 80° C. and 150° C. or about 90° C. to 140° C. In embodiments, the reaction is carried out under a reduced pressure to facilitate removal of water formed in the ketalization or acetalization reaction. It is also possible to employ molecular sieves, superabsorbents, or some other means for removal of water from the reaction mixture. If the reaction is carried out under reduced pressure, temperatures of less than about 150° C. can be employed in some embodiments. The reaction can also be carried out at temperatures above about 200° C., however, in some embodiments this can result in an increased amount of side products.

The reaction can be carried out in the presence of an additional solvent that is substantially inert under reaction conditions, such as aliphatic or aromatic hydrocarbons, ethers or chlorinated hydrocarbons. Such solvents can also be used with the method of the invention to remove water formed during the reaction by an azeotropic distillation. In embodiments, toluene, benzene or another inert solvent could be used. The reaction can also be carried out in the presence of a reactive solvent. The reactive solvent is, in some embodiments, a solvent that is known to form an azeotrope with water. For example, the inclusion of an amount of toluene in the reaction mixture can enable the distillation of water evolved from the reaction at a lower temperature than that of water alone. In other embodiments, the reactive solvent is an alcohol that forms a first ketal or acetal, followed by replacement with the desired alcohol to form the product ketal or acetal. For example, inclusion of a small amount of methanol or ethanol in the reaction to form an end product that is the 1:1 adduct of ethylene glycol and a pyruvate ester can results in a fast reaction rate of initial 2:1 adduct formation, followed by formation of the 1:1 adduct formation. Where the alcohol is capable of forming an azeotrope with water, the presence of the alcohol can further accelerate the reaction, reduce the temperature required to remove water, or both.

In embodiments, the reaction of glycerol with an alkyl levulinate is carried out employing the method of the invention. In such embodiments, unreacted glycerol or alkyl levulinate can be removed from the reaction pot by distillation. Glycerol has been found to codistill with alkyl levulinates where the ester alkyl is a lower alkyl, such as methyl, ethyl, propyl, or n-butyl. Thus, in embodiments, reactions according to the method of the invention and employing a molar excess of alkyl levulinate facilitates removal of incidental unreacted glycerol. The recovered mixture of glycerol and levulinic ester is, in embodiments, reused in the synthesis of an additional quantity of ketal ester.

In embodiments where glycerol is reacted with an alkyl levulinate to give the corresponding ketal, it has been found that water codistills with alkyl levulinates where the ester alkyl group is a lower alkyl, such as methyl, ethyl, propyl, or n-butyl. In some embodiments, these codistillates can be distilled under reduced pressure. Thus, in embodiments, water formed during the ketalization of an alkyl levulinate can be conveniently removed from the reaction mixture, during the reaction by distillation with excess alkyl levulinate. This use of the alkyl levulinate is advantageously employed, for example, where a molar excess of alkyl levulinate is employed in the reaction mixture. In some such embodiments, water is separated from the codistillate after codistillation. After separation of water from the codistillate, the alkyl levulinate is, in embodiments, returned to the vessel containing the reaction mixture. In some embodiments, the alkyl levulinate is further subjected to drying operations to remove water prior to being returned to the reaction mixture. Nonlimiting examples of drying operations are fractional distillation, mixing the codistillate with molecular sieves, selective membrane filtration, dialysis, or any other technique known in the art for drying materials. In some embodiments, the alkyl levulinate gathered from the codistillate is set aside and used in a subsequent reaction mixture, for example in a batch type reaction.

In some embodiments, improved miscibility of alcohol and keto acid, semialdehyde, or ester thereof is achieved by maintaining, or adding, an amount of the 1:1 adduct or the 2:1 adduct product in the reaction vessel. For example, glycerol has been found to have a considerable solubility in its 1:1 adduct with of ethyl levulinate at elevated temperatures, for example at temperatures above about 60° C. Thus, the reaction mixture of glycerol and ethyl levulinate is advantageously carried out in the presence of some amount of its 1:1 adduct. In embodiments, about 10 to 50 wt % of the 1:1 adduct of ethyl levulinate and glycerol is employed in the reaction mixture to maintain miscibility of glycerol and ethyl levulinate in the absence of further cosolvents. In other embodiments, about 25 to 30 weight % of the 1:1 adduct of glycerol and ethyl levulinate is employed in the reaction mixture to maintain miscibility of glycerol and ethyl levulinate in the absence of further cosolvents. Other reagents have varying miscibility and thus it will be understood by the skilled artisan that varying ratios of 1:1 adduct or 2:1 adduct are advantageously employed in some embodiments of the method of the invention to produce partial or complete miscibility of reagents in the reaction vessel. For example, in some embodiments, 1 wt % of a 1:1 adduct is sufficient to obtain miscibility at the desired reaction temperature. In other embodiments, as much as 75 wt % of a 1:1 adduct or 2:1 adduct is required to achieve miscibility of the reagents. However, it should be understood that even in embodiments where miscibility is not achieved, the method of the reaction is sufficient to bring about the reaction to form 1:1 adducts and 2:1 adducts as described above.

The process of making a ketal or acetal employing the method of the invention can be carried out in a batch operation, in a continuous operation, or in a semi-continuous operation. The reagents and acid catalyst in the present invention are, in embodiments, mixed during the reaction by employing any of a variety of techniques known in the art. For example, mechanical mixing by a propeller, impeller, or a mechanical agitator such as a shaker, roller, or tumbler can be used. Passive mixing, such as by a static mixer, may also be employed. In some embodiments, the reagents and an acid catalyst are mixed in a reactor with active or passive mixing, optionally including some quantity of the product ketal or acetal to aid in miscibility. In some embodiments, the reaction mixture is heated and a vacuum optionally applied to remove substantially all water formed in the reaction. In some embodiments, the water is removed by distillation; in other embodiments water is removed by distillation of its azeotrope with the keto acid, semiacetal, or ester thereof; in still other embodiments, the water is removed by including molecular sieves, superabsorbent materials, or another means of removing water within the reaction vessel itself. In some embodiments, the resulting product mixture containing the ketal or acetal product, excess keto acid, semialdehyde, or ester thereof, and acid catalyst is further subjected to a distillation to remove excess keto acid, semialdehyde, or ester thereof, and further to distill out a majority of the product ketal or acetal. The distillation can be carried out in a batch process or in a continuous fashion, using one of devices known in the art, such as batch or continuous feed distillation columns, wiped film evaporators, spinning film evaporators, rotary evaporators, falling film evaporators and other similar equipment. In embodiments, the ketal or acetal with acid catalyst remaining in the reaction vessel is subsequently re-used by mixing with additional fresh reagents.

By employing various embodiments of the method of the invention, the desired ketal or acetal product of keto acid, semialdehyde, or ester thereof can be obtained at about 90% or greater based on the theoretical yield, as measured by GC-MS or $H^1$ NMR. In other embodiments about 95% or greater based on the theoretical yield is obtained. In still other embodiments, about 98% or greater yield based on theoretical yield is obtained. In still other embodiments, about 9% or greater yield based on theoretical yield is obtained. The presence of side products is, in embodiments, less than about 5% of the desired ketal or acetal, as measured by GC-MS or $H^1$ NMR. In other embodiments, the presence of side products is less than about 2% of the desired ketal or acetal. In still other embodiments, the presence of side products is less than about 1% of the desired ketal or acetal.

In some embodiments, reactions carried out employing the method of the invention, the reaction is at least about 90% complete in about 24 hours or less of reaction time as determined by GC-MS or $H^1$ NMR. In other embodiments, the reaction is at least about 95% complete in about 24 hours of reaction time or less. In other embodiments, the reaction is at least about 95% complete in about 4 hours of reaction time or less. In other embodiments, the reaction is at least about 95% complete in about 2 hours of reaction time or less. In other embodiments, the reaction is at least about 95% complete in about 1 hour of reaction time or less. In other embodiments, the reaction is at least about 95% complete in about 20 minutes of reaction time or less. In still other embodiments, the reaction is at least about 98% complete in about 20 minutes of reaction time or less.

Purification of the products of the reactions carried out employing the method of the invention can be accomplished by a variety of known means. The methods of the invention are not particularly limited by the means to remove residual impurities from the reaction mixtures. In some embodiments distillation, particularly by wiped film evaporation or falling film evaporation, are employed to remove unreacted keto acid, semialdehyde, or ester thereof; or unreacted alcohol; or other impurities such as minor amounts of water. In other embodiments, insoluble matrix materials, typically porous solids such as activated carbon, molecular sieves, ion exchange resins, and the like are used to purify the products of the reactions. The insoluble matrix materials may be slurried with the reaction products or placed in a column or bed and the products of the reaction contacted with the matrix materials in a continuous operation. In some embodiments, residual alcohols or polyols are removed from the reaction mixture via an ion exchange resin comprising sulfonate moieties. Without limiting the method of the invention, it is postulated that in some embodiments, alcoholic compounds undergo hydrogen bonding with the sulfonate moieties that are covalently bound to the matrix, and the alcohols are thereby removed from the reaction products. Examples of useful ion exchange resins include LEWATIT® 202, sold by the Lanxess Company of Pittsburgh, Pa.; and AMBERLITE™ BD10DRY™, sold by the Rohm and Haas Company of Philadelphia, Pa.

In other embodiments, the reaction product may be purified by distillation using standard techniques. However, the heat of distillation can, in some embodiments, cause the formation of oligomerized or transesterified products of the desired ketals and acetals. This is true, for example, in some embodiments where acids such as sulfuric acid or hydrochloric acid are employed in the reaction, because these acids remain in the reaction product when the reaction is completed. In some such embodiments, these side products are undesirable. In such embodiments, the acid catalyst products of the ketalization reaction can be neutralized prior to distillation in order to reduce or eliminate the byproducts caused by the combination of heat and acid. For example, prior to distillation, the reaction product is neutralized by the addition of a neutralizing agent that is a buffer, a weak base, or a strong base. It is advantageous, in some embodiments, to adjust the amount of base added so that the acid is neutralized but no additional base is added. This avoids the formation of side products attributable to base catalysis, such as side products due to transesterification.

Examples of useful neutralizing agents include basic alumina, magnesia, carbonates such as sodium carbonate, calcium carbonate, or monobasic sodium or potassium carbonate, calcium triphosphate, ammonia, anion exchange resins, calcium oxide, calcium hydroxide, potassium or sodium phosphate, and hydroxyapatite. In some embodiments the neutralizing agent is bound to a solid support, such as activated carbon or molecular sieves. The amount of neutralizing agent employed in the method of the invention depends on the type of neutralizing agent and the amount of acid in the reaction product; for example, in the case of a strong base such as sodium hydroxide, it is necessary to calculate acid equivalents in the reaction product and add the same number of equivalents of base in order to neutralize the acid without addition of excess neutralizing agent. In embodiments where, for example, a buffering agent is employed instead of a strong base, it is advantageous to add about 1 wt % to 50 wt %, or about 5 wt % to 25 wt %, or about 10 wt % of the buffering agent to the reaction product based on the weight of reaction product. The neutralization agent is, in embodiments, a solid that provides a heterogeneous mixture with the reaction product and is easily separated from the reaction product by filtration after neutralization is complete.

The following Examples further elucidate and describe the method of the invention without limiting the scope thereof.

EXPERIMENTAL SECTION

Experimental Materials (A) Ethyl levulinate (Aldrich)
(B) Ethyl levulinate (Aldrich), distilled
(C) Ethyl levulinate (Aldrich), distilled and treated with LEWATIT® GF 505 resin
(D) Ethyl levulinate (Aldrich), neutralized with 10 wt % (N)
(E) Glycerol (Acros) (% chlorides=0.012)
(F) Sulfuric acid (Aldrich) 95-98%
(G) Trimethylol propane (Aldrich)
(H) Concentrated HCl (Fisher)
(I) Ethylene glycol (Aldrich)
(J) Methyl acetoacetate (Aldrich)
(K) Sulfamic acid (Fisher)
(L) Phosphoric acid (85 wt %) (Fisher)
(M) Amberlyst® 15 (Rohm and Haas)
(N) Basic Alumina (Aldrich)
(O) 1:1 adduct of ethyl levulinate and glycerol, distilled (product of Example 2)
(P) Glycerol (Aldrich) (% chlorides=0.012)
(Q) 1:1 adduct of ethyl levulinate and glycerol Example 1

The acid number of ethyl levulinate (A) was measured using ASTM D664-07. The resulting measurement is shown in Table 1. The acid number was also converted to molar equivalents of acetic acid per mole of levulinic acid and is shown as % acid in Table 1.

Ethyl levulinate (A) was then distilled using standard laboratory techniques, resulting in ethyl levulinate (B). The acid number of (B) was also measured using ASTM D664-07, and the % acid was calculated based on this number as for (A); this value is shown in Table 1.

Subsequently, ethyl levulinate (B) was passed through a column of LEWATIT® GF 505 medium-basic anion exchange resin (obtained from the Lanxess Company of Pittsburgh, Pa.) to result in ethyl levulinate (C). Acid number of ethyl levulinate (C) was measured using ASTM D664-07, and the % acid was calculated based on this number as for (A); this value is shown in Table 1.

Ethyl levulinate (A) was stirred in a flask with 10 wt % of basic alumina (M) for one hour, followed by filtration to remove the basic alumina, resulting neutralized ethyl levulinate (D). Acid number of ethyl levulinate (D) was measured using ASTM D664-07, and the % acid was calculated based on this number as for (A); this value is shown in Table 1.

TABLE 1

Acid number and molar equivalents of acetic acid in ethyl levulinate samples.

| Reagent | Acid Number (mg KOH/g sample) | Acetic acid, g per g Reagent | Acetic acid, mol equiv. per mol Reagent |
|---|---|---|---|
| (A) | 0.99 | 0.00107 | 0.00257 |
| (B) | 0.34 | 0.00033 | 0.00079 |
| (C) | 0.08 | 0.00009 | 0.00022 |
| (D) | 0.00 | 0 | 0 |

Example 2

A 3-neck, 500 mL round bottom flask was charged with 90.02 g (0.53 moles) of (C) and 12.87 g (0.14 moles) of (E). The contents of the flask were observed to consist of a heterogeneous mixture of two liquid phases. The flask was equipped with an overhead mechanical stirrer, a Dean-Stark separator with an overhead condenser, and a thermocouple extending below the surface of the flask contents. The contents of the flask were blanketed with a nitrogen stream and heated to 110° C. while stirring. Once the contents were at 110° C., 1.33 µL ($2.5 \times 10^{-5}$ moles) of (H) was added into the flask below the surface of the contents by pipette. The contents of the flask began to bubble. The initial pressure in the flask was set to 300 Torr, and pressure was then ramped from 300 Torr to about 30 Torr over about 7 min. The contents of the flask were stirred for an additional 13 min at 25-30 Torr. During this time, a distillate was collected in the Dean Stark separator. The distillate was observed to separate as it cooled. A sample of the reaction mixture was removed for GC-MS analysis.

The GC-MS analysis was carried out according to standard laboratory techniques. The integration peak areas of all peaks in the chromatogram were automatically calculated by an Agilent Technologies ChemStation (Agilent Technologies of Santa Clara, Calif.). The calculated peak areas were reported as a weighted percent (expressed as abundance) relative to the area of all of the peaks in the chromatogram (total area). The GC portion of the analysis is shown in FIG. 1. No glycerol (0.0%) was detected in the analysis, indicating 100% conversion. FIG. 1 also shows the absence of products attributable from side reactions. Comparison of the trace shown in FIG. 1 to one taken at time zero was not done, because the initial reaction mixture was heterogeneous.

Examples 3-38

The procedure according to Example 2 was used to produce the data shown in Table 2. The catalyst identity, catalyst concentration, reactants, ratio of reactants, reaction temperature, and reaction time was varied as shown. In each of the reactions except Examples 25-27, GC-MS was utilized to measure percent conversion and the amount of transesterification side-reactions similarly to Example 2.

Examples 25-27 employed ethylene glycol, which could not be assayed by GC-MS due to its volatility. These reactions were instead analyzed by $^1$H NMR. The products formed in Example 26 could not be analyzed by $^1$H NMR due to the large proportion of transesterification products: the peaks corresponding to the transesterification products interfered with peaks corresponding to the 1:1 adduct.

Examples 3 to 38 show that a relatively low number of equivalents of acid catalyst, for example $1 \times 10^{-4}$ equivalents of acid catalyst, per mole of limiting reagent, produced high yield of the desired 1:1 adducts at relatively fast reaction times without the formation of transesterification side products. Similarly, a high molar ratio of keto ester to alcohol produced low levels of transesterification, and fast reaction rate to form the desired 1:1 adducts. When very low acid catalyst levels were combined with reagent ratios of at least about 2.5 or more moles of keto ester per mole of alcohol, the reaction was consistently fast and clean, providing high yields of the desired ketal with minimum side reaction products formed.

TABLE 2

Ratios of reagents, reaction variables, and reaction products for various ketal syntheses.

| Example No. | Reagent 1, moles | Reagent 2, moles | Catalyst, moles | Reaction Temp., °C. | Reaction Time, min. | % Limiting Reagent (GC-MS) | % Transesterification products (GC-MS) | % Ketal product (GC-MS) | Molar equiv. catalyst added per mole limiting reagent | Total acid = [(Mol equiv. acid added) + (mol equiv. acetic acid from Reagent 1)] per mole limiting reagent |
|---|---|---|---|---|---|---|---|---|---|---|
| 3 | (B) 0.53 | (E) 0.14 | (F) $2.5 \times 10^{-5}$ | 110 | 26 | 0 | 0 | 100 | $1.8 \times 10^{-4}$ | $3.1 \times 10^{-3}$ |
| 4 | (A) 2.95 | (E) 0.56 | (F) $3.0 \times 10^{-3}$ | 80 | 20 | 0 | 3.2 | 96.8 | $5.3 \times 10^{-3}$ | $1.9 \times 10^{-2}$ |
| 5 | (A) 2.95 | (E) 0.56 | (F) $3.0 \times 10^{-4}$ | 80 | 20 | 0 | 0.04 | 99.96 | $5.3 \times 10^{-4}$ | $1.4 \times 10^{-2}$ |
| 6 | (A) 2.95 | (E) 0.56 | (F) $5.9 \times 10^{-5}$ | 80 | 20 | 0 | 0 | 100 | $1.1 \times 10^{-4}$ | $1.3 \times 10^{-2}$ |
| 7 | (A) 2.95 | (E) 0.56 | (F) $3.0 \times 10^{-5}$ | 80 | 20 | 0 | 0 | 100 | $5.4 \times 10^{-5}$ | $1.4 \times 10^{-2}$ |
| 8 | (A) 0.66 | (E) 1.12 | (F) $6.7 \times 10^{-5}$ | 80 | 110 | 8.8 | 0 | 91.2 | $1.0 \times 10^{-3}$ | $3.6 \times 10^{-3}$ |
| 9 | (A) 0.97 | (E) 0.55 | (F) $9.7 \times 10^{-5}$ | 80 | 85 | 0.1 | 0.9 | 99.0 | $1.8 \times 10^{-3}$ | $6.3 \times 10^{-3}$ |

TABLE 2-continued

Ratios of reagents, reaction variables, and reaction products for various ketal syntheses.

| Example No. | Reagent 1, moles | Reagent 2, moles | Catalyst, moles | Reaction Temp., °C. | Reaction Time, min. | % Limiting Reagent (GC-MS) | % Transesterification products (GC-MS) | % Ketal product (GC-MS) | Molar equiv. catalyst added per mole limiting reagent | Total acid = [(Mol equiv. acid added) + (mol equiv. acetic acid from Reagent 1)] per mole limiting reagent |
|---|---|---|---|---|---|---|---|---|---|---|
| 10 | (A) 0.66 | (E) 0.56 | (F) $6.7 \times 10^{-5}$ | 80 | 82 | 2.4 | 0.6 | 97.0 | $1.2 \times 10^{-3}$ | $4.2 \times 10^{-3}$ |
| 11 | (A) 1.64 | (E) 0.56 | (F) $2.5 \times 10^{-5}$ | 80 | 54 | 0 | 0 | 100 | $4.0 \times 10^{-5}$ | $7.6 \times 10^{-3}$ |
| 12 | (A) 2.3 | (E) 0.56 | (F) $1.4 \times 10^{-4}$ | 75 | 26 | 0.2 | 0 | 99.8 | $2.5 \times 10^{-4}$ | $1.1 \times 10^{-2}$ |
| 13 | (A) 1.64 | (E) 0.56 | (F) $2.5 \times 10^{-4}$ | 80 | 14 | 0.4 | 0.07 | 99.5 | $4.5 \times 10^{-4}$ | $8.0 \times 10^{-3}$ |
| 14 | (A) 2.95 | (E) 0.56 | (F) $2.5 \times 10^{-5}$ | 80 | 15 | 0.2 | 0 | 99.8 | $4.0 \times 10^{-5}$ | $1.4 \times 10^{-2}$ |
| 15 | (A) 2.95 | (E) 0.56 | (F) $3.0 \times 10^{-5}$ | 100 | 11 | 0 | 0 | 100 | $5.0 \times 10^{-5}$ | $1.4 \times 10^{-2}$ |
| 16 | (A) 2.95 | (E) 0.56 | (F) $5.9 \times 10^{-5}$ | 100 | 18 | 0 | 0 | 100 | $1.1 \times 10^{-4}$ | $1.4 \times 10^{-2}$ |
| 17 | (A) 1.64 | (E) 0.56 | (F) $3.0 \times 10^{-5}$ | 100 | 27 | 0.2 | 0.03 | 99.8 | $5.0 \times 10^{-5}$ | $7.6 \times 10^{-3}$ |
| 18 | (A) 1.64 | (E) 0.56 | (F) $5.9 \times 10^{-5}$ | 100 | 45 | 0.1 | 0 | 99.9 | $1.1 \times 10^{-4}$ | $7.6 \times 10^{-3}$ |
| 19 | (B) 0.63 | (E) 0.14 | (H) $2.5 \times 10^{-5}$ | 110 | 30 | 0 | 0 | 100 | $1.8 \times 10^{-4}$ | $3.7 \times 10^{-3}$ |
| 20 | (B) 0.63 | (E) 0.14 | (H) $2.5 \times 10^{-3}$ | 110 | 30 | 0 | 0.2 | 99.8 | $4.5 \times 10^{-3}$ | $8.0 \times 10^{-3}$ |
| 21 | (B) 2.5 | (G) 0.56 | (F) $2.5 \times 10^{-5}$ | 110 | 60 | 0.3 | 0 | 99.7 | $4.0 \times 10^{-5}$ | $3.6 \times 10^{-3}$ |
| 22 | (B) 2.5 | (G) 0.56 | (F) $2.5 \times 10^{-3}$ | 110 | 60 | 0.2 | 13.5 | 86.3 | $4.5 \times 10^{-3}$ | $8.0 \times 10^{-3}$ |
| 23 | (B) 2.0 | (G) 1.0 | (F) $2.5 \times 10^{-5}$ | 110 | 60 | 6.0 | 0.1 | 93.9 | $3.0 \times 10^{-5}$ | $1.6 \times 10^{-3}$ |
| 24 | (B) 2.0 | (G) 1.0 | (F) $2.5 \times 10^{-5}$ | 110 | 120 | 2.8 | 0.2 | 97.0 | $3.0 \times 10^{-5}$ | $1.6 \times 10^{-3}$ |
| 25 | (B) 0.63 | (I) 0.14 | (F) $2.5 \times 10^{-5}$ | 80 | 120 | 11.7[a] | 0[a] | 88.3 | $1.8 \times 10^{-4}$ | $3.7 \times 10^{-3}$ |
| 26 | (B) 0.63 | (I) 0.14 | (F) $2.5 \times 10^{-3}$ | 80 | 120 | n/a[b] | 7.2[b] | n/a[b] | $1.8 \times 10^{-2}$ | $2.2 \times 10^{-2}$ |
| 27 | (B) 0.28 | (E) 0.14 | (F) $2.5 \times 10^{-5}$ | 80 | 120 | 17.5[a] | 0.3[a] | 82.2[a] | $1.8 \times 10^{-4}$ | $1.8 \times 10^{-3}$ |
| 28 | (B) 0.63 | (E) 0.14 | (K) $2.5 \times 10^{-5}$ | 110 | 30 | 0 | 0 | 100 | $1.8 \times 10^{-4}$ | $3.7 \times 10^{-3}$ |
| 29 | (B) 0.28 | (E) 0.14 | (K) $2.5 \times 10^{-5}$ | 110 | 164 | 0.04 | 0 | 99.96 | $1.8 \times 10^{-4}$ | $1.7 \times 10^{-3}$ |
| 30 | (B) 0.28 | (E) 0.14 | (L) $3.0 \times 10^{-5}$ | 110 | 20 | 1.1 | 0 | 98.9 | $2.1 \times 10^{-4}$ | $1.8 \times 10^{-3}$ |
| 31 | (B) 0.28 | (E) 0.14 | (L) $3.0 \times 10^{-4}$ | 110 | 20 | 1.2 | 0 | 98.8 | $2.1 \times 10^{-3}$ | $3.7 \times 10^{-3}$ |
| 32 | (J) 0.63 | (E) 0.14 | (F) $2.5 \times 10^{-5}$ | 80 | 100 | 0.04 | 11.5 | 88.5 | $1.8 \times 10^{-4}$ | $3.7 \times 10^{-3}$ |
| 33 | (J) 0.28 | (E) 0.14 | (F) $2.5 \times 10^{-5}$ | 80 | 100 | 0.1 | 7.6 | 92.3 | $1.8 \times 10^{-4}$ | $1.8 \times 10^{-3}$ |
| 34 | (D) 0.28 | (E) 0.14 | (M) $2.4 \times 10^{-5}$ | 110 | 135 | 0 | 1.3 | 98.7 | $3.3 \times 10^{-4}$ | $3.3 \times 10^{-4}$ |
| 35 | (D) 1.26 | (E) 0.28 | (M) $2.5 \times 10^{-5}$ | 110 | 60 | 0 | 0 | 100 | $1.8 \times 10^{-4}$ | $1.8 \times 10^{-4}$ |
| 36 | (D) 0.28 | (E) 0.14 | (K) $2.0 \times 10^{-5}$ | 110 | 164 | 2.7 | 0 | 93.3 | $1.8 \times 10^{-4}$ | $1.8 \times 10^{-4}$ |
| 37 | (D) 1.26 | (P) 0.28 | (F) $5 \times 10^{-5}$ | 110 | 24 | 0 | 0 | 100 | $1.7 \times 10^{-4}$ | $1.7 \times 10^{-4}$ |
| 38 | (D) 1.26 | (P) 0.28 | (F) $5 \times 10^{-4}$ | 110 | 24 | 0 | 10.0 | 90.0 | $1.7 \times 10^{-3}$ | $1.7 \times 10^{-3}$ |

[a] Ethylene glycol was not visible by GC-MS due to its volatility. $^1$H NMR was used to determine conversion.

[b] Due to the large amount of transesterified byproducts, the amount of residual ethylene glycol could not be determined by $^1$H NMR. The amount of transesterified byproducts was determined by GC-MS.

Figure 2:
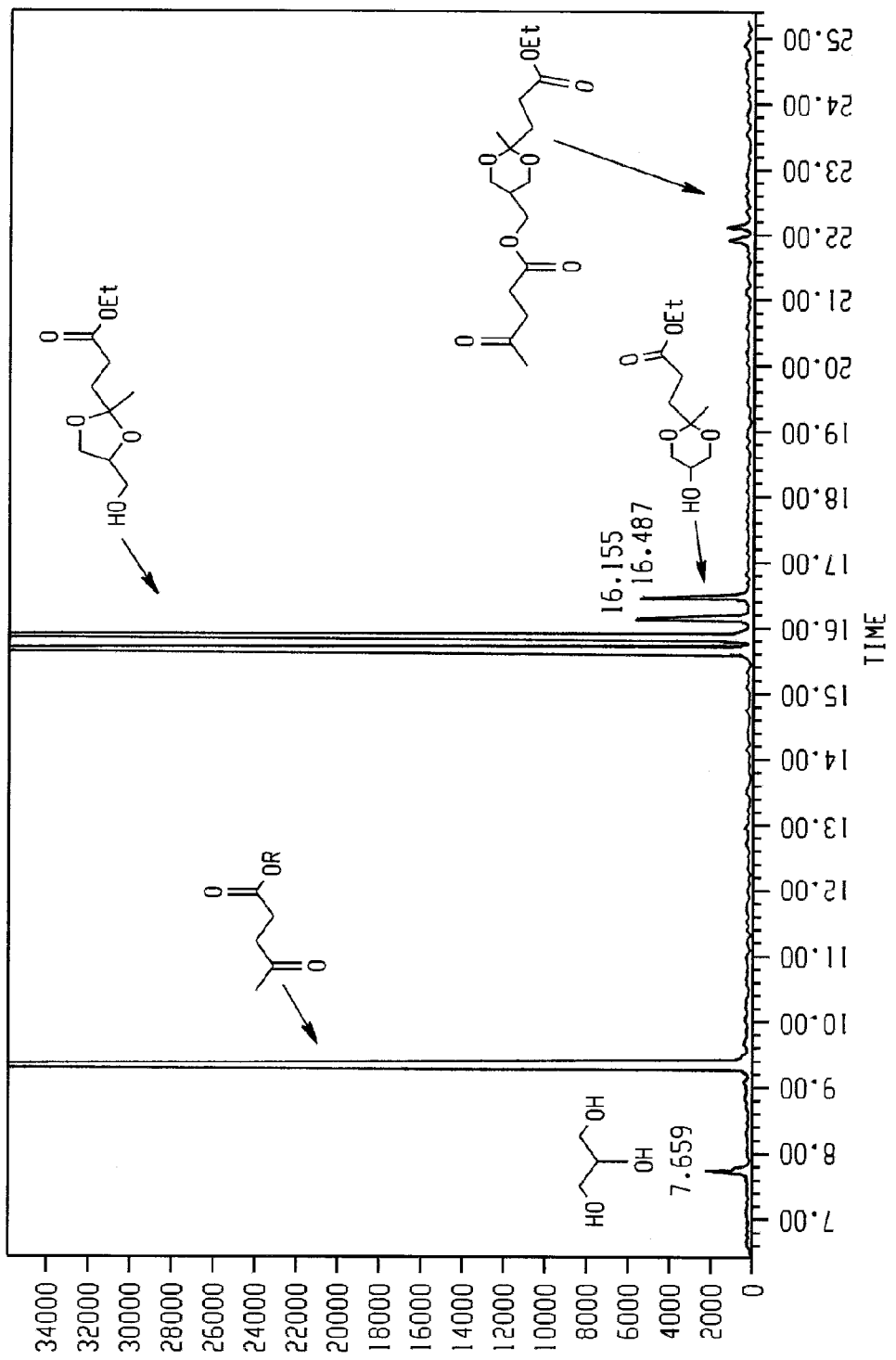
FIG. 2 is the GC portion of a GC-MS of the reaction mixture at the end of the reaction corresponding to Example 17.

FIG. 2 shows a GC trace of the GC-MS performed at the end of the reaction time of Example 17. The transesterification products quantified in Table 2 above can be observed in the GC trace.

Figure 3:
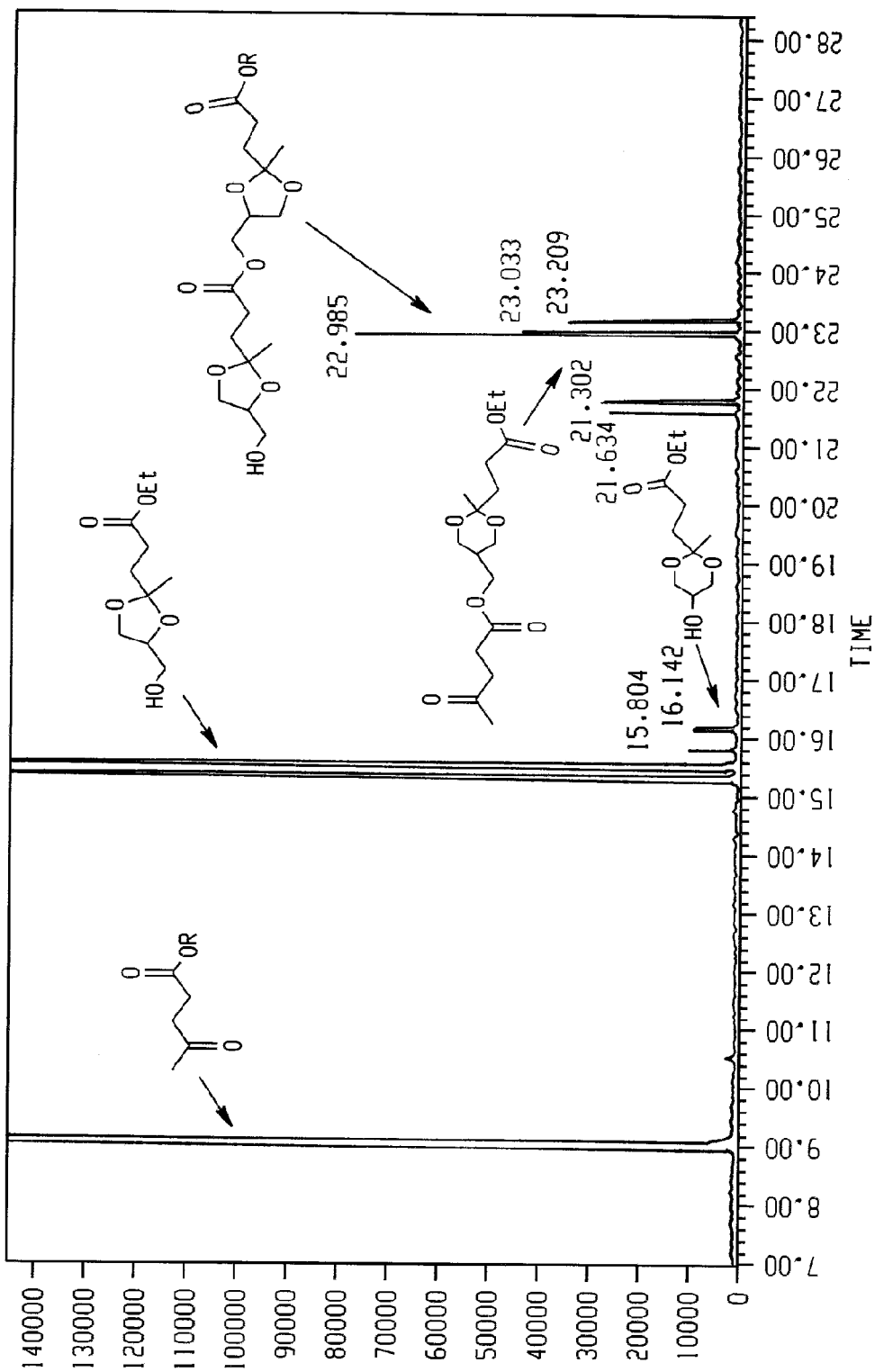
FIG. 3 is the GC portion of a GC-MS of the reaction mixture at the end of the reaction corresponding to Example 38.

FIG. 3 shows a GC trace of the GC-MS performed at the end of the reaction time of Example 9. The presence of a substantial amount of transesterification products is clearly visible in the spectrum.

Example 39

Into a glass scintillation vial was added 8.66 g (0.06 mol) of (C) and 1.87 g (0.02 mol) of (E) for a total reaction mixture weight of 10.53 g. The mixture was observed to be heterogeneous, having two liquid phases existing as droplets of compound (E) dispersed in compound (A). A 5.0 g aliquot of (O), as formed in Example 2, was added and the mixture heated to 98° C. At that temperature, the mixture was clear and appeared to be a single phase. The total mixture weight was 15.53 g: 5.0 g of (O), 8.66 g (A), and 1.87 g (E); or 32.1 wt % of (O).

The mixture was cooled down to 80° C. at which point the solution became cloudy. An additional 0.5 g of compound (O) was added, and the mixture was again observed to be clear and homogeneous. The total mixture weight at 80° C. was 16.03 g: 5.5 g of (O), 8.66 g (A), and 1.87 g (E), or 34.3 wt % of (O).

Example 40

Lewatit 202 resin (obtained from Lanxess Corporation of Pittsburgh, Pa.) was washed with 2-4 bed volumes of anhydrous methanol in a glass column, and then placed into a vacuum oven set to 60-80° C. until dry.

A 1000 mL round bottom flask was charged with 500 g of (Q) containing 4600 ppm by weight glycerol as determined by gas chromatography using flame ionization detector (GC-FID). The flask was equipped with a magnetic stirrer, a thermocouple, and a nitrogen inlet/outlet. To the flask was added 50 g of the washed and dried Lewatit 202 resin. The contents of the flask were heated to 60° C. with stirring. After one hour, a sample removed from the flask contained non-detectable levels of glycerol as measured by GC-FID with a known glycerol calibration curve capable of detecting 1 ppm glycerol.

Example 41

A 2 inch diameter glass column was packed with 8 inches of Lewatit 202 that was washed and dried as above, and 50 g of (Q) containing 8271 ppm by weight glycerol as measured by $^1$H NMR was eluted through the column by gravity. Samples of eluted liquid were taken throughout the experiment for analysis. The first eluted sample consisted of (Q) with 194 ppm glycerol as measured by $^1$H NMR, and all subsequent eluted samples contained (Q) and non-detectable levels of glycerol as measured by $^1$H NMR.

Examples 42-45

Using the procedure described in Example 2, 425.32 g (2.50 mol) (B), 51.13 g (0.56 mol) (E), and 1.3 μl (2.5×10$^{-5}$ mol) (F) were reacted. The reaction product was determined by GC-MS to be 66% ethyl levulinate and 33% of the glycerol ketal of ethyl levulinate. The reaction product had an initial oligomer content of approximately 0.9% according to the total % area of the GC-MS peaks for oligomer products. The reaction product was acidic due to the fact that the sulfuric acid catalyst had not been removed, nor had any other trace acids been removed.

A 60 g aliquot of the reaction product was placed into a 100 mL round bottom flask. The flask was placed onto a rotary evaporator and heated in an oil bath set to 110-115° C. with an applied vacuum of about 40-45 Torr. A first liquid was observed to distill from the reaction product. When the distillation stopped, the temperature of the oil bath was raised to 175° C. and a second liquid was distilled. The distillation was complete when no further liquid could be distilled from the flask. The final contents of undistilled material weighed 5.1 g, and the contents were black and nearly opaque. The oligomer content of the undistilled liquid was measured to be 64% by GPC. This indicated that the total oligomer content rose from 0.9% to 5.4% in the 60 g aliquot of crude reaction product after it was heated and distilled.

This result is shown in Table 3 as Example 42.

A 120 g aliquot of the reaction product and 1.2 g of NaHCO$_3$ (obtained from Acros Organics of Geel, Belgium) were placed in a 250 mL round bottom flask. The contents of the flask were stirred for 1 h. The contents were decanted from the solid base. A 60 g aliquot of the decanted liquid was placed into a 100 mL flask. The flask was placed onto a rotary evaporator and heated in an oil bath set to 110-115° C. with an applied vacuum of about 40-45 Torr. A first liquid was observed to distill from the reaction product. When the distillation stopped, the temperature of the oil bath was raised to 175° C. and a second liquid was distilled. The distillation was complete when no further liquid could be distilled from the flask. The final contents of undistilled material weighed 1.8 g, and the contents were brown and transparent. The oligomer content of the undistilled liquid was measured to be 46% by GPC. This indicated that the total oligomer content rose from 0.9% to 1.4% in the 60 g aliquot of crude reaction product after it was heated and distilled. The result is shown in Table 3 as Example 43.

The procedure of Example 43 was repeated using Na$_2$HPO$_4$ (obtained from Fisher Scientific of Waltham, Mass.) in place of NaHCO$_3$. The result is shown in Table 3 as Example 44.

The procedure of Example 43 was repeated using K$_3$PO$_4$ (obtained from Fisher Scientific) in place of NaHCO$_3$. The result is shown in Table 3 as Example 45.

TABLE 3

Effect of base or buffers added to crude reaction product glycerol ketal of ethyl levulinate prior to heating and distilling.

| Example | Neutralization agent | Weight % Neutralization agent/Buffer | % Oligomer products before purification (GC-MS) | % Oligomer products in distillation bottoms/wt. of original sample (GPC) |
|---|---|---|---|---|
| 42 | none | 0 | 0.9 | 5.4 |
| 43 | NaHCO$_3$ | 1 | 0.9 | 1.4 |

TABLE 3-continued

Effect of base or buffers added to crude reaction product glycerol ketal of ethyl levulinate prior to heating and distilling.

| Example | Neutralization agent | Weight % Neutralization agent/Buffer | % Oligomer products before purification (GC-MS) | % Oligomer products in distillation bottoms/wt. of original sample (GPC) |
|---|---|---|---|---|
| 44 | $Na_2HPO_4$ | 1 | 0.9 | 0.6 |
| 45 | $K_3PO_4$ | 1 | 0.9 | 7.3 |

Examples 46-47

Using the procedure described in Example 2, 1377.4 g (7.33 mol) of butyl levulinate (obtained from Langfang Triple Well Chemicals Company, Ltd. Of Langfang City, HeBei, China), 245.6 g (2.67 mol) (E), and 25.38 μl (4.8×10⁻⁴ mol) (F) were reacted. The reaction product was determined by GC-MS to be 61.4% butyl levulinate and 37.6% of the glycerol ketal of butyl levulinate. The reaction product had an initial oligomer content of approximately 1.0% according to the total % area of the GC-MS peaks for oligomer products. The reaction product was acidic due to the fact that the sulfuric acid catalyst had not been removed, nor had any other trace acids been removed.

A 583.35 g aliquot of the reaction product was placed into a 1 liter, 3-neck roundbottom flask equipped with a thermocouple, a magnetic stirrer, and a distillation column with 3 receiving flasks. All distillable liquids were removed under vacuum of 35 Torr over a temperature range of about 110° C. to 210° C. After the distillation, 133.74 g of undistilled bottoms remained in the flask. The oligomer content of the undistilled bottoms was measured by GC and the final oligomer content had risen from 1.0% to 10.2%. The yield of undistilled bottoms was 22.9% of the total weight of the total reaction product prior to distillation.

A 930.2 g aliquot of the reaction product and 93.0 g of (N) were placed into a 2 liter Erlenmeyer flask and stirred for 1 hour. The mixture was filtered to remove the solids and 832.32 g of the filtrate was transferred into a 1 liter 3-neck roundbottom flask equipped with a thermocouple, a magnetic stirrer, and a distillation column with 3 receiving flasks. All distillable liquids were removed under vacuum of 35 Torr over a temperature range of about 110° C. to 210° C. After the distillation, 47.06 g of undistilled bottoms remained in the flask. The oligomer content of the distillation bottoms was measured by GC and the final oligomer content had risen from 1.0% to 5.6%. The yield of undistilled bottoms was 5.7% of the total weight of the total reaction product prior to distillation.

The various embodiments described above are provided by way of illustration only and should not be construed to limit the claims attached hereto. The present invention may suitably comprise, consist of, or consist essentially of, any of the disclosed or recited elements. Thus, the invention illustratively disclosed herein can be suitably practiced in the absence of any element which is not specifically disclosed herein. Various modifications and changes will be recognized that may be made without following the example embodiments and applications illustrated and described herein, and without departing from the true spirit and scope of the following claims.

What is claimed:

1. A method of preparing a compound of formula (3)

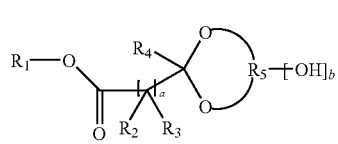

(3)

wherein $R_1$, $R_2$, and $R_3$ are independently hydrogen, a linear alkyl group, a branched alkyl group, a cyclic alkyl group, a linear alkenyl group, a branched alkenyl group, a cyclic alkenyl group, an aryl group, or alkaryl group, each of which groups optionally comprises one or more heteroatoms independently chosen from oxygen, nitrogen, halogen atoms, sulfur, silicon, and phosphorus;

$R_4$ is a linear alkyl group, a branched alkyl group, a cyclic alkyl group, a linear alkenyl group, a branched alkenyl group, a cyclic alkenyl group, an aryl group, or alkaryl group, each of which groups optionally comprises one or more heteroatoms independently chosen from oxygen, nitrogen, halogen atoms, sulfur, silicon, and phosphorus;

a is 0 or an integer from 1 to 12;

b is 0 or an integer; and $R_5$ is a residue of a polymeric polyol, a hydroxyl functionalized surface, a silane, a siloxane, a silanol, or a hydrocarbon group having the formula:

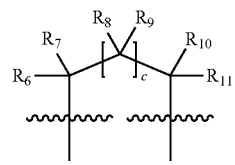

wherein c is 0 or 1 and $R_6$, $R_7$, $R_8$, $R_9$, $R_{10}$, and $R_{11}$ are independently hydrogen, a linear alkyl group, a branched alkyl group, a cyclic alkyl group, a linear alkenyl group, a branched alkenyl group, a cyclic alkenyl group, an aryl group, or an alkaryl group, each of which groups optionally comprises one or more heteroatoms;

the method comprising:
a) providing a reaction mixture comprising
i. a compound of formula (2)

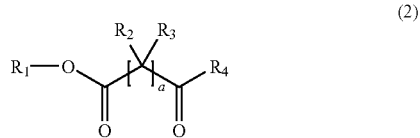

wherein $R_1$, $R_2$, $R_3$, $R_4$, and a are as defined above,
ii. a compound of formula (4)

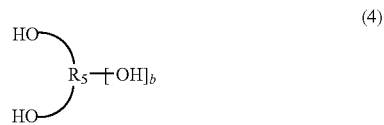

wherein $R_5$ and b are as defined above, and
iii. $1 \times 10^{-6}$ to $1 \times 10^{-3}$ molar equivalents, based on moles of compound (4), of an acid catalyst; and
b) reacting compounds (2) and (4);
wherein less than 5% of compound (2) undergoes an esterification or transesterification reaction, as measured by GC-MS.

2. The method of claim 1, wherein the compound (2) is provided at 2.5 molar equivalents or greater based on moles of compound (4).

3. The method of claim 1, further comprising removing water.

4. The method of claim 1, wherein the reacting comprises heating the reaction mixture at a temperature and pressure sufficient to distill water, a water co-distillate, or a water-containing azeotrope.

5. The method of claim 1, further comprising
neutralizing the acid catalyst by adding a neutralizing agent to the reaction mixture, the neutralizing agent comprising a metal oxide, a metal carbonate, a metal phosphate, a metal hydroxide, or an anion exchange resin, and
subsequently separating compound (3) from the neutralized reaction mixture.

6. The method of claim 1, wherein the acid catalyst is provided at $1 \times 10^{x6}$ to $1 \times 10^{-4}$ molar equivalents based on moles of compound (4).

7. The method of claim 6, further comprising separating the compound (3) from the reaction mixture by distillation, wherein the separating is carried out without neutralization or removal of the acid catalyst.

8. The method of claim 1, wherein the acid catalyst is provided at $1 \times 10^{-5}$ to $1 \times 10^{-4}$ molar equivalents based on moles of compound (4).

9. The method of claim 1, wherein the acid catalyst comprises a solid support comprising sulfonic acid groups covalently bonded to the solid support, the solid support comprising crosslinked styrene-divinyl benzene resin.

10. The method of claim 1, wherein at least about 95% of compound (4) is converted to compound (3) as measured by GC-MS.

11. The method of claim 1, wherein the compound of formula (2) is ethyl levulinate or butyl levulinate.

12. The compound of claim 1, wherein the compound of formula (4) is glycerol or 1,2-propanediol.

13. The method of claim 1, wherein the compound of formula (2) is ethyl levulinate or butyl levulinate; the compound of formula (4) is glycerol or 1,2-propanediol and the ethyl levulinate or butyl levulinate is present in an amount from about 3 to about 6 molar equivalents, based on moles of glycerol.

14. A method of preparing a compound of formula (3)

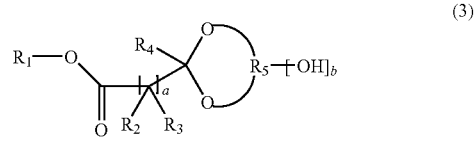

wherein
$R_1$, $R_2$, $R_3$, and $R_4$ are independently hydrogen, a linear alkyl group, a branched alkyl group, a cyclic alkyl group, a linear alkenyl group, a branched alkenyl group, a cyclic alkenyl group, an aryl group, or an alkaryl group, each of which groups optionally comprises one or more heteroatoms independently chosen from oxygen, nitrogen, halogen atoms, sulfur, silicon, and phosphorus;

a is 0 or an integer from 1 to 12;

b is 0 or an integer; and $R_5$ is a residue of a polymeric polyol, a hydroxyl functionalized surface, a silane, a siloxane, a silanol, or a hydrocarbon group having the formula

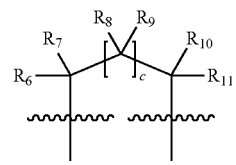

wherein c is 0 or 1, and $R_6$, $R_7$, $R_8$, $R_9$, $R_{10}$, and $R_{11}$ are independently hydrogen, a linear alkyl group, a branched alkyl group, a cyclic alkyl group, a linear alkenyl group, a branched alkenyl group, a cyclic alkenyl group, an aryl group, or an alkaryl group, each of which groups optionally comprises one or more heteroatoms independently chosen from oxygen, nitrogen, halogen atoms, sulfur, silicon, and phosphorus;

the method comprising:
a) providing a reaction mixture comprising
i. about 2.5 molar equivalents or greater, based on moles of compound (4), of a compound of formula (2)

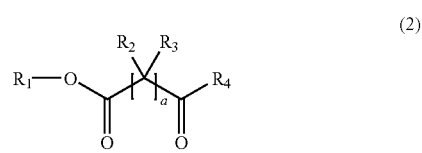

wherein $R_1$, $R_2$, $R_3$, $R_4$, and a are as defined above, and
ii. about 1 molar equivalent of a compound of formula (4)

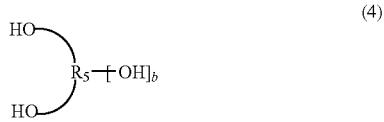

wherein $R_5$ and b are as defined above, and
iii. $1\times10^{-6}$ to $5\times10^{-3}$ molar equivalents of an acid catalyst based on moles of compound (4); and
b) reacting compounds (2) and (4),
wherein less than 5% of compound (2) undergoes an esterification or transesterification reaction as measured by GC-MS.

15. The method of claim 14, further comprising removing water.

16. The method of claim 14, wherein the reacting comprises heating the reaction mixture at a temperature and pressure sufficient to distill water, a water co-distillate, or a water-containing azeotrope.

17. The method of claim 14, further comprising neutralizing the acid catalyst by adding a neutralizing agent to the reaction mixture, the neutralizing agent comprising a metal oxide, a metal carbonate, a metal phosphate, a metal hydroxide, or an anion exchange resin, and
subsequently separating compound (3) from the neutralized reaction mixture.

18. The method of claim 14, wherein the acid catalyst is provided at $1\times10^{-6}$ to $1\times10^{-4}$ molar equivalents based on moles of compound (4).

19. The method of claim 18, further comprising separating the compound (3) from the reaction mixture by distillation, wherein the separating is carried out without neutralization or removal of the acid catalyst.

20. The method of claim 14, wherein the acid catalyst is provided at $1\times10^{-5}$ to $1\times10^{-4}$ molar equivalents based on moles of compound (4).

21. The method of claim 14, wherein the acid catalyst comprises a solid support comprising sulfonic acid groups covalently bonded to the solid support, the solid support comprising crosslinked styrene-divinyl benzene resin.

22. The method of claim 14, wherein at least about 95% of compound (4) is converted to compound (3) as measured by GC-MS.

23. The method of claim 14, wherein the compound of formula (2) is ethyl levulinate or butyl levulinate.

24. The compound of claim 14, wherein the compound of formula (4) is glycerol or 1,2-propanediol.

25. The method of claim 14, wherein the compound of formula (2) is ethyl levulinate or butyl levulinate; the compound of formula (4) is glycerol or 1,2-propanediol and the ethyl levulinate or butyl levulinate is present in an amount from about 3.5 to about 6 molar equivalents, based on moles of glycerol.

26. A method of preparing a cyclic ketal of levulinic acid or an ester thereof, the method comprising:
a. providing a reaction mixture comprising
  i. glycerol,
  ii. about 2.5 to 5 molar equivalents, based on moles of glycerol, of an alkyl levulinate selected from the group consisting of ethyl levulinate and butyl levulinate, and
  iii. $1\times10^{-6}$ to $1\times10^{-3}$ molar equivalents, based on moles of glycerol, of an acid catalyst selected from sulfuric acid, sulfamic acid, and a sulfonic acid; and
b. collecting a cyclic ketal of levulinic acid or ester thereof;
wherein less than 5% of the alkyl levulinate undergoes an esterification or transesterification reaction, as determined by GC-MS.

27. The method of claim 26, further comprising, prior to collecting the cyclic ketal,
heating the reaction mixture to about 80° C. to 140° C.;
adjusting the pressure of the reaction mixture to about 10 to 50 Torr;
distilling a codistillate comprising water, levulinate ester, and ethanol for a period of about 10 to 60 minutes; and
removing excess levulinate ester by distillation.

28. The method of claim 27, wherein the alkyl levulinate is ethyl levulinate and the temperature is between about 90° C. and 120° C.

29. The method of claim 27, further comprising adding a neutralizing agent to the reaction mixture prior to distilling, the neutralizing agent comprising a metal oxide, a metal carbonate, a metal phosphate, a metal hydroxide, or an anion exchange resin.

30. A method of preparing a cyclic ketal of levulinic acid or an ester thereof with a polyol, the method comprising:
a. providing a reaction mixture comprising
  i. 1,2-propanediol;
  ii. about 2.5 to 5 molar equivalents, based on moles of 1,2-propanediol, of an alkyl levulinate selected from the group consisting of ethyl levulinate and butyl levulinate, and
  iii. $1\times10^{-6}$ to $1\times10^{-3}$ molar equivalents, based on moles of 1,2-propanediol, of an acid catalyst selected from sulfuric acid, sulfamic acid, and a sulfonic acid; and
b. collecting a cyclic ketal of levulinic acid or ester thereof;
wherein less than 5% of the alkyl levulinate undergoes an esterification or transesterification reaction, as determined by GC-MS.

31. The method of claim 30, further comprising, prior to collecting the cyclic ketal,
heating the reaction mixture to about 80° C. to 140° C.;
adjusting the pressure of the reaction mixture to about 10 to 50 Torr;
distilling a codistillate comprising water, levulinate ester, and ethanol for a period of about 10 to 60 minutes; and
removing excess levulinate ester by distillation.

32. The method of claim 31, wherein the alkyl levulinate is ethyl levulinate and the temperature is between about 90° C. and 120° C.

33. The method of claim 31, further comprising adding a neutralizing agent to the reaction mixture prior to distilling, the neutralizing agent comprising a metal oxide, a metal carbonate, a metal phosphate, a metal hydroxide, or an anion exchange resin.

34. The method of claim 1, wherein less than 2% of compound (2) undergoes an esterification or transesterification, as measured by GC-MS.

35. The method of claim 1, wherein less than 1% of compound (2) undergoes an esterification or transesterification, as measured by GC-MS.

36. The method of claim 10, wherein at least about 95% of compound (4) is converted to compound (3) as measured by GC-MS over a period equal to or less than 2 hours.

37. The method of claim 10, wherein at least about 98% of compound (4) is converted to compound (3) as measured by GC-MS over a period equal to or less than 30 minutes.

38. The method of claim 14, wherein less than 2% of compound (2) undergoes an esterification or transesterification, as measured by GC-MS.

39. The method of claim 14, wherein less than 1% of compound (2) undergoes an esterification or transesterification, as measured by GC-MS.

40. The method of claim 14, wherein at least about 95% of compound (4) is converted to compound (3) as measured by GC-MS over a period equal to or less than 4 hours.

41. The method of claim 21, wherein at least about 98% of compound (4) is converted to compound (3) as measured by GC-MS over a period equal to or less than 2 hours.

42. The method of claim 26, wherein less than 2% of the alkyl levulinate undergoes an esterification or transesterification, as measured by GC-MS.

43. The method of claim 26, wherein less than 1% of the alkyl levulinate undergoes an esterification or transesterification, as measured by GC-MS.

44. The method of claim 26, wherein at least about 95% of glycerol is converted to a cyclic ketal of levulinic acid or ester thereof as measured by GC-MS over a period equal to or less than 2 hours.

45. The method of claim 26, wherein at least about 98% of glycerol is converted to a cyclic ketal of levulinic acid or ester thereof as measured by GC-MS over a period equal to or less than 30 minutes.

46. The method of claim 26, wherein the acid catalyst is sulfuric acid or sulfamic acid.

\* \* \* \* \*